US005670330A

United States Patent [19]
Sonenberg et al.

[11] Patent Number: 5,670,330
[45] Date of Patent: Sep. 23, 1997

[54] ANTI-TUMOR AGENT ASSAY USING PKR

[75] Inventors: Nahum Sonenberg, Cote St. Luc, Canada; Michael G. Katze, Seattle, Wash.; Sophie Roy, Mount Royal; Antonis E. Koromilas, Montreal, both of Canada; Glen H. Barber, Seattle, Wash.

[73] Assignees: McGill University, Canada; University of Washington, Seattle, Wash.

[21] Appl. No.: 143,219

[22] Filed: Oct. 25, 1993

Related U.S. Application Data

[63] Continuation-in-part of Ser. No. 141,244, Oct. 22, 1993, abandoned, which is a continuation-in-part of Ser. No. 953,681, Sep. 29, 1992, abandoned.

[51] Int. Cl.⁶ .................................................. C12Q 1/48
[52] U.S. Cl. ................................... 435/15; 435/4; 435/6
[58] Field of Search ............................. 435/15, 4, 6

[56] References Cited

U.S. PATENT DOCUMENTS 5,362,623  11/1994  Vogelstein et al. ...................... 435/6

OTHER PUBLICATIONS

Chen et al., "Cloning of the cDNA of the Heme-Regulated Eukaryotic Initiation Factor 2α (eIF-2α) Kinase of Rabbit Reticulocytes: Homology to Yeast GCN2 Protein Kinase and Human Double-Stranded-RNA-Dependent eIF-2α Kinase," 88 *Proc. Natl. Acad. Sci. USA* 7729, 1991.

Chong et al., "Human p68 Kinase Exhibits Growth Suppression in Yeast and Homology to the Translational Regulator GCN2," 11 *The EMBO Journal* 1553, 1992.

Etkind and Krug, "Purification of Influenza Viral Complementary RNA: Its Genetic Content and Activity in Wheat Germ Cell-Free Extracts," 16 *J. of Virology* 1464, 1975.

Feng et al., "Identification of Double-Stranded RNA-Binding Domains in the Interferon-Induced Double-Stranded RNA-Activated p68 Kinase," 89 *Proc. Natl. Acad. Sci. USA* 5447, 1992.

Winn-Deen et al., "Sensitive Fluorescence Method for Detecting DNA Ligation Amplification Products," *Clin. Chem.* 1522, 1991.

Winter et al., "A Method to Detect and Characterize Point Mutations in Transcribed Genes: Amplification and Overexpression of the Mutant c-Ki-ras Allele in Human Tumor Cells," 82 *Proc. Natl. Acad. Sci. USA* 7575, 1985.

Galabru and Hovanessian, "Autophosphorylation of the Protein Kinase Dependent on Double-Stranded RNA," 262 *J. Biol. Chem.* 15538, 1987.

Galabru et al., "The Binding of Double-Stranded RNA and Adenovirus VAI RNA to the Interferon-Induced Protein Kinase," 178 *Eur. J. Biochem.* 581, 1989.

Hanks et al., "Protein Kinase Catalytic Domain Sequence Database: Identification of Conserved Features of Primary Structure and Classification of Family Members," 200 *Methods Enzymol.* 38, 1991.

Harlow et al., *Antibodies: A Laboratory Manual*, (Cold Spring Harbor Laboratories, 1988) pp. 423–470, 93–115, 271–318.

Katze et al., "Functional Expression and RNA Binding Analysis of the Interferon-Induced, Double-Stranded RNA-Activated, 68,000-$M_1$ Protein Kinase in a Cell-Free System," 11 *Mol. Cell. Biol.* 5497, 1991.

Koromilas et al., "Malignant Transformation by a Mutant of the IFN-Inducible dsRNA-Dependent Protein Kinase," 257 *Science* 1685, 1992.

Laurent et al., "Monoclonal Antibodies to an Interferon-Induced $M_r$ 68,000 Protein and Their Use for the Detection of Double-Stranded RNA-Dependent Protein Kinase in Human Cells," 82 *Proc. Natl. Acad. Sci. USA* 4341, 1985.

Laurent et al., "Characterisation of the Interferon-Mediated Protein Kinase by Polyclonal Antibodies," 125 *Biochem. Biophys. Res. Comm.* 1, 1984.

Link et al., "Purified $I_KB$–β Is Inactivated Upon Dephosphorylation," 267 *J. Biol. Chem.* 239, 1992.

Melton et al., "Functional Messenger RNAs are Produced by SP6 In Vitro Transcription of Cloned cDNAs," 12 *Nucleic Acids Res.* 7057, 1984.

Meyers et al., "Detection of Single Base Substitutions by Ribonuclease Cleavage at Mismatches in RNA:DNA Duplexes," 230 *Science* 1242, 1985.

Petryshyn et al., "Detection of Activated Double-Stranded RNA-Dependent Protein Kinase in 3T3-F442A Cells," 85 *Proc. Natl. Acad. Sci. USA* 1427, 1988.

Petryshyn et al., "Growth-Related Expression of a Double-Stranded RNA-Dependent Protein Kinase in 3T3 Cells," 259 *J. Biol. Chem.* 14736, 1984.

Ramirez et al., "Ribosome Association of GCN2 Protein Kinase, a Translational Activator of the GCN4 Gene of Saccharomyces Cerevisiae," 11 *Mol. Cell. Biol.* 3027, 1991.

Sanger et al., "DNA Sequencing with Chain-Terminating Inhibitors," 74 *Proc. Natl. Acad. Sci. USA* 5463, 1977.

Huang, P. et al. (1991) "Differential responses of HUT 78 variants to the antiproliferative influence of interferon (IFN)–alpha 2A" Clinical Research 39(3):747A Oct. 1991.

Chong, K.L. et al. (1992) "Human p68 kinase exhibits growth suppression in yeast and homology to the translation regulator GCN2" *EMBO J.* 11(4):1553–1562.

(List continued on next page.)

*Primary Examiner*—Robert A. Wax
*Assistant Examiner*—Kawai Lau
*Attorney, Agent, or Firm*—Pennie & Edmonds

[57] ABSTRACT

A method of screening human tissue for the presence of neoplastic cells, by determining the activity of PKR, P58 of anti-P58 in test cells being screened, and identifying candidate neoplastic cells on the basis of subnormal PKR, P58, or anti-P58 activity. The activities may be determined directly by measuring protein kinase activity or its equivalent, or measured indirectly, by detecting functional mutations in the various proteins. Also disclosed are assay kits for carrying out the screening method.

9 Claims, 12 Drawing Sheets

OTHER PUBLICATIONS

Colson, G. et al. (1992) "Mode of action of the antitumor compound girodazole" *Biochem. Pharm.* 43(8):1717–1723.

Haines et al. "Cellular and Enzymatic Activities of a Synthetic Heteropolymer Double-Stranded RNA of Defined Size" J. Biol. Chem. 267(26):18315–9 Sep. 15, 1992.

Kimchi et al. "Kinetics of the Induction of Three Translation-Regulatory Enzymes by Interferon" Proc. Natl. Acad. Sci., USA 76(7):3208–12 (Jul. 1979).

Gresser and Tovey "Antitumor Effects of Interferon" Biochem. et Biophys. Acta 516:231–247 (1978).

Lee, et al. "Characterization and Regulation of the 58,000–Dalton Cellular Inhibitor of the Interferon–Induced, dsRNA-Activated Protein Kinase" J. Biol. Chem. 267(20):14238–43 Jul. 1992.

Samuel et al, "Purification of Double-Stranded RNA-Dependent Protein Kinase From Mouse Fibroblasts" Meth. Enz. 119:499–517 (1986).

Charcosset et al. "Effects of 9–OH–Ellipticine on Cell Survival, Macromolecular Syntheses, and Cell Cycle Progression in Sensitive and Resistant Chinese Hamster Lung Cells" Can. Res. 45:4229–36 (1985).

DeClercq, Erik. "Effect of Mouse Interferon and Polyriboinosinic Acid–Polyribocytidilic Acid on L–Cell Tumor Growth in Nude Mice" Can. Res. 37:1502–6 (1977).

```
 -115         CGGCCCGAGCGAGAGCAGACTGCGGGCGGGCGGCCGCAGCTGCAGCCTGAGCGCC
  -60   GCGGCGGGGGGCTGGTGGGCCCCGCAGCTTTGCTCCTCCTCTGCGCCCGCGCTCTCGGAC
    1   ATGGTGGCCCCCGGCTCTGTGACCAGCCGGCTGGGCTCGGTGTTCCCTTTCCTGCTGGTC
        M   V   A   P   G   S   V   T   S   R   L   G   S   V   F   P   F   L   L   V    20
   61   CTGGTGGACCTGCAGTACGAAGGTGCTGAATGTGGAGTAAATGCAGATGTTGAGAAGCAT
        L   V   D   L   Q   Y   E   G   A   E   C   G   V   N   A   D   V   E   K   H    40
  121   CTGGAATTGGGCAAGAAGCTGCTCGCAGCCGGACAGCTCGCGGATGCGTTATCTCAGTTT
        L   E   L   G   K   K   L   L   A   A   G   Q   L   A   D   A   L   S   Q   F    60
  181   CACGCTGCAGTAGATGGTGACCCTGATAACTATATTGCTTACTATCGGAGAGCTACTGTC
        H   A   A   V   D   G   D   P   D   N   Y   I   A   Y   Y   R   R   A   T   V    80
  241   TTTTTAGCTATGGGCAAATCAAAAGCAGCACTTCCTGATTTAACTAAAGTGATTGAATTG
        F   L   A   M   G   K   S   K   A   A   L   P   D   L   T   K   V   I   E   L   100
  301   AAGATGGATTTCACTGCAGCAAGATTACAGAGAGGTCACTTATTACTCAAACAAGGAAAA
        K   M   D   F   T   A   A   R   L   Q   R   G   H   L   L   L   K   Q   G   K   120
  361   CTTGATGAAGCAGAAGATGATTTTAAAAAAGTGCTCAAGTCAAATCCAAGTGAAAATGAA
        L   D   E   A   E   D   D   F   K   K   V   L   K   S   N   P   S   E   N   E   140
  421   GAGAAGGAGGCCCAGTCCCAGCTTGTCAAATCTGATGAAATGCAGCGTCTGCGCTCACAA
        E   K   E   A   Q   S   Q   L   V   K   S   D   E   M   Q   R   L   R   S   Q   160
  481   GCACTGGATGCCTTTGAGAGCTCAGATTTTACTGCTGCTATAACCTTCCTTGATAAGATT
        A   L   D   A   F   E   S   S   D   F   T   A   A   I   T   F   L   D   K   I   180
  541   TTAGAGGTTTGTGTTTGGGATGCAGAACTTCGAGAACTTCGAGCTGAATGTTTTATAAAA
        L   E   V   C   V   W   D   A   E   L   R   E   L   R   A   E   C   F   I   K   200
  601   GAAGGGGAACCTAGGAAAGCGATAAGTGACTTAAAAGCTTCATCAAAATTGAAAAACGAT
        E   G   E   P   R   K   A   I   S   D   L   K   A   S   S   K   L   K   N   D   220
  661   AATACTGAGGCATTTTATAAAATCAGCACACTCTACTATGAACTAGGAGACCATGAACTG
        N   T   E   A   F   Y   K   I   S   T   L   Y   Y   E   L   G   D   H   E   L   240
  721   TCTCTCAGTGAAGTTCGTGAATGTCTTAAACTTGACCAGGATCATAAAAGGTGTTTTGCA
        S   L   S   E   V   R   E   C   L   K   L   D   Q   D   H   K   R   C   F   A   260
  781   CACTATAAACAAGTAAAGAAACTGAATAAGCTGATTGAGTCAGCTGAAGAGCTCATCAAA
        H   Y   K   Q   V   K   K   L   N   K   L   I   E   S   A   E   E   L   I   K   280
  841   GAAGGCAGGTACACAGATGCAATCAGCAAATATGAATCTGTCATGAAAACAGAGCCAGGT
        E   G   R   Y   T   D   A   I   S   K   Y   E   S   V   M   K   T   E   P   G   300
  901   GTTCATGAATATACAATTCGTTCAAAAGAAAGGATTTGCCACTGCTTTTCTAAGGATGAG
        V   H   E   Y   T   I   R   S   K   E   R   I   C   H   C   F   S   K   D   E   320
  961   AAGCCTGTTGAAGCTATTCGAGTATGTTCAGAAGTTTTACAGGTGGAACCTGACAACGTG
        K   P   V   E   A   I   R   V   C   S   E   V   L   Q   V   E   P   D   N   V   340
 1021   AATGCTCTGAAAGACCGAGCAGAGGCCTATTTAATAGAAGAAATGTATGATGAAGCTATT
        N   A   L   K   D   R   A   E   A   Y   L   I   E   E   M   Y   D   E   A   I   360
 1081   CAGGATTATGAAACTGCTCAGGAACACAATGAGAATGATCAGCAGATTCGAGAAGGTCTG
        Q   D   Y   E   T   A   Q   E   H   N   E   N   D   Q   Q   I   R   E   G   L   380
 1141   GAGAAAGCACAGAGGCTACTGAAACAGTCACAGAGACGAGATTATTACAAAATCTTGGGA
        E   K   A   Q   R   L   L   K   Q   S   Q   R   R   D   Y   Y   K   I   L   G   400
 1201   GTAAAAAGAAATGCCAAAAAGCAAGAAATCATTAAAGCATACCGAAAATTAGCACTGCAG
```

FIG.10A

```
            V  K  R  N  A  K  K  Q  E  I  I  K  A  Y  R  K  L  A  L  Q   420
1261  TGGCACCCAGACAACTTCCAGAACGAAGAAGAAAAGAAAAAAGCTGAGAAGAAGTTCATT
            W  H  P  D  N  F  Q  N  E  E  E  K  K  K  A  E  K  K  F  I   440
1321  GACATAGCAGCTGCTAAAGAAGTCCTCTCCGATCCAGAAATGAGGAAGAAGTTTGATGAC
            D  I  A  A  A  K  E  V  L  S  D  P  E  M  R  K  K  F  D  D   460
1381  GGAGAAGACCCCCTGGACGCAGAGAGCCAACAAGGAGGTGGCGGCAACCCTTTCCACAGG
            G  E  D  P  L  D  A  E  S  Q  Q  G  G  G  N  P  F  H  R   480
1441  AGCTGGAACTCATGGCAAGGGTTCAGTCCCTTTAGCTCAGGCGGACCTTTTAGATTTAAA
            S  W  N  S  W  Q  G  F  S  P  F  S  S  G  G  P  F  R  F  K   500
1501  TTCCACTTCAATTAAACCAGCTGTTTTTCTGCAGAAAAAAAAAAAAAAAAAAAAAAAAAA
            F  H  F  N  ***
1561  AAAAAAAAAAAA
```

FIG.10B

5'-
ACCAGCTGTTTTTCTGCTCCTCTTCCTTCATTTTTTAAAGTTTTAAAACAAACAAAATAACCTTGTTCCGGG
ATCCTATTGAAAAAGAAAATTCAAATCTTTCAGTTTGTCCACGACCAAAGAGGTGTTCAGAATGGCAGTGTC
TGTTCTTATTCATTGCAGACTTGAGGCTGATGGGGGTGAGGGCAGGGAGGCAGGTGGGCTTCTGTTTCTGGC
AGAGCAGCCTGTGTCTGTGCTGTGACCGGATGGAAGCAGCAGTCTGAGGCAGGTGCACAGATCTTTTATCTT
CTACACTGGAGCAGGTGAGATTCTCTTCTTGTTGCATACGTGTCAGCACCTGCGTGTGTGAGGAGGAGCCTG
GGCTGTCAGCATTCTCCAAGAGGAATGACCCTTCTGAGCTGTATGTTCTTAGGCACAACTTGGCTTCGACTC
TGGTCTGTCCGGTCACCTGTCACTATGTTCTTAGGCACAACTTGGCTTCGACTCTGGTCTGTCCGGTCACCT
GTCACTATGTTACATTTCCACTTGCGTTCCCATCTCTTGCTGAGCATGAACGTGGCTGCTGTTGAAGGTGGC
AGAGCCCTTAGAGAACCTGCTACGAATGGCAGGGTGAGGTCTGGTAAATACGTATTTTTTTTGTTCAGTACC
TGAAGGAGAATACTGAAAACAATATTAAATACAATGAACTAAAAATATGTAAAATAAGTTCAGATAACATAG
CAGTGGTATTTAAATAATATTGCTGTAGTACAGAATTAACAACTGAAGTTGTGAGTTGTTACAGCATTTCCT
GTGGCAGGATTGGCTTAGAATGTAAAGTTGCTCAGTCAACATAGACAGTATGCCATGTCTCCCACTTTTGGT
AAGTTCAGCAGCTTCTCTTACGTCCTGGCCTCCCTGGCCCGTGGGTGCCCACGTGGGACTGCTTTGAGGTGG
GTGTTAAGTAGCAGGCCTCCCCTTTACAGACCTTGATGCCTCTGGAAGTTCTGCCAGGAAAGAAACAGGTTT
ACAGACCTAGTGAGCTCTGGCTGTATGTCCACTATCAAGATAGCATCTCTTTTTGGGATACCTTCTTACCTT
TTAAGAAAAATGAAACTATTCAGTCTTTATATGCTGGATAATTTTTTCCTTAAAAGAAAAATAAGTGTTAAT
CTATAACATTAAATATTTATGGATAGGGATTCCATAAAATATTATGGAACTATTGATGCTGCATTTAAAATC
TAAGAATTATTTAGATAAAATTATTACCTTTATTCTAGAAAGGTTTTGTGTTTTTTTTTTTGCCTCAGAACA
TTTTGACAATTTAAGTAGGATGGGCCTAATATACTGACTGCTTTTTGGGAAATCAAGCATCTTCTGAGTTGT
TGGGGCTGTCCTACCACTAATATCCACAACCAGCCAGCCAAGCACAAATAGTTTCCTTCTACAGTCATTCTG
AAACATACTTGGAAAAGTTTTTTAATCTGAGGGACAAAAACAAAATAGTTGAGTTGGACACAACACGTTAAA
TGCTTTTTGCATCTATTTAGAAGTTTATTTCTTTCC<u>AATAAA</u>CAAGATGGCATTTTGAAACTAAAAAAAAAA
AAAAAAAAAAAAAAA -3'

FIG.10C

SEQUENCE LISTING ( 1 ) GENERAL INFORMATION:

( i i i ) NUMBER OF SEQUENCES: 27

( 2 ) INFORMATION FOR SEQ ID NO:1:

( i ) SEQUENCE CHARACTERISTICS:
        ( A ) LENGTH: 2628 base pairs
        ( B ) TYPE: nucleic acid
        ( C ) STRANDEDNESS: double ( D ) TOPOLOGY: linear ( i i ) MOLECULE TYPE: DNA (genomic)

( i i i ) HYPOTHETICAL: NO ( v i ) ORIGINAL SOURCE:
    ( C ) INDIVIDUAL ISOLATE: HUMAN PKR GENE, FIGURE 5

( i x ) FEATURE:
    ( A ) NAME/KEY: CDS
    ( B ) LOCATION: 187..1836

( x i ) SEQUENCE DESCRIPTION: SEQ ID NO:1:

```
CAGTTTCTGG AGCAAATTCA GTTTGCCTTC CTGGATTTGT AAATTGTAAT GACCTCAAAA          60

CTTTAGCAGT TCTTCCATCT GACTCAGGTT TGCTTCTCTG GCGGTCTTCA GAATCAACAT         120

CCACACTTCC GTGATTATCT GCGTGCATTT TGGACAAAGC TTCCAACCAG GATACGGGAA         180

GAAGAA ATG GCT GGT GAT CTT TCA GCA GGT TTC TTC ATG GAG GAA CTT            228
       Met Ala Gly Asp Leu Ser Ala Gly Phe Phe Met Glu Glu Leu
         1               5                  10

AAT ACA TAC CGT CAG AAG CAG GGA GTA GTA CTT AAA TAT CAA GAA CTG           276
Asn Thr Tyr Arg Gln Lys Gln Gly Val Val Leu Lys Tyr Gln Glu Leu
 15          20                  25                  30

CCT AAT TCA GGA CCT CCA CAT GAT AGG AGG TTT ACA TTT CAA GTT ATA           324
Pro Asn Ser Gly Pro Pro His Asp Arg Arg Phe Thr Phe Gln Val Ile
             35                  40                  45

ATA GAT GGA AGA GAA TTT CCA GAA GGT GAA GGT AGA TCA AAG AAG GAA           372
Ile Asp Gly Arg Glu Phe Pro Glu Gly Glu Gly Arg Ser Lys Lys Glu
             50                  55                  60

GCA AAA AAT GCC GCA GCC AAA TTA GCT GTT GAG ATA CTT AAT AAG GAA           420
Ala Lys Asn Ala Ala Ala Lys Leu Ala Val Glu Ile Leu Asn Lys Glu
         65                  70                  75

AAG AAG GCA GTT AGT CCT TTA TTA TTG ACA ACA ACG AAT TCT TCA GAA           468
Lys Lys Ala Val Ser Pro Leu Leu Leu Thr Thr Thr Asn Ser Ser Glu
 80                  85                  90

GGA TTA TCC ATG GGG AAT TAC ATA GGC CTT ATC AAT AGA ATT GCC CAG           516
Gly Leu Ser Met Gly Asn Tyr Ile Gly Leu Ile Asn Arg Ile Ala Gln
 95                 100                 105                 110

AAG AAA AGA CTA ACT GTA AAT TAT GAA CAG TGT GCA TCG GGG GTG CAT           564
Lys Lys Arg Leu Thr Val Asn Tyr Glu Gln Cys Ala Ser Gly Val His
             115                 120                 125

GGG CCA GAA GGA TTT CAT TAT AAA TGC AAA ATG GGA CAG AAA GAA TAT           612
Gly Pro Glu Gly Phe His Tyr Lys Cys Lys Met Gly Gln Lys Glu Tyr
             130                 135                 140

AGT ATT GGT ACA GGT TCT ACT AAA CAG GAA GCA AAA CAA TTG GCC GCT           660
Ser Ile Gly Thr Gly Ser Thr Lys Gln Glu Ala Lys Gln Leu Ala Ala
             145                 150                 155

AAA CTT GCA TAT CTT CAG ATA TTA TCA GAA GAA ACC TCA GTG AAA TCT           708
Lys Leu Ala Tyr Leu Gln Ile Leu Ser Glu Glu Thr Ser Val Lys Ser
 160                 165                 170

GAC TAC CTG TCC TCT GGT TCT TTT GCT ACT ACG TGT GAG TCC CAA AGC           756
Asp Tyr Leu Ser Ser Gly Ser Phe Ala Thr Thr Cys Glu Ser Gln Ser
175                 180                 185                 190

AAC TCT TTA GTG ACC AGC ACA CTC GCT TCT GAA TCA TCA TCT GAA GGT           804
Asn Ser Leu Val Thr Ser Thr Leu Ala Ser Glu Ser Ser Ser Glu Gly
             195                 200                 205

GAC TTC TCA GCA GAT ACA TCA GAG ATA ATC TAC AGT GAC AGT TTA AAC           852
Asp Phe Ser Ala Asp Thr Ser Glu Ile Ile Tyr Ser Asp Ser Leu Asn
             210                 215                 220

AGT TCT TCG TTG CTT ATG AAT GGT CTC AGA AAT AAT CAA AGG AAG GCA           900
Ser Ser Ser Leu Leu Met Asn Gly Leu Arg Asn Asn Gln Arg Lys Ala
         225                 230                 235
```

```
AAA AGA TCT TTG GCA CCC AGA TTT GAC CTT CCT GAC ATG AAA GAA ACA        948
Lys Arg Ser Leu Ala Pro Arg Phe Asp Leu Pro Asp Met Lys Glu Thr
240             245                 250

AAG TAT ACT GTG GAC AAG AGG TTT GGC ATG GAT TTT AAA GAA ATA GAA        996
Lys Tyr Thr Val Asp Lys Arg Phe Gly Met Asp Phe Lys Glu Ile Glu
255             260                 265                 270

TTA ATT GGC TCA GGT GGA TTT GGC CAA GTT TTC AAA GCA AAA CAC AGA       1044
Leu Ile Gly Ser Gly Gly Phe Gly Gln Val Phe Lys Ala Lys His Arg
                275                 280                 285

ATT GAC GGA AAG ACT TAC GTT ATT AAA CGT GTT AAA TAT AAT AAC GAG       1092
Ile Asp Gly Lys Thr Tyr Val Ile Lys Arg Val Lys Tyr Asn Asn Glu
            290                 295                 300

AAG GCG GAG CGT GAA GTA AAA GCA TTG GCA AAA CTT GAT CAT GTA AAT       1140
Lys Ala Glu Arg Glu Val Lys Ala Leu Ala Lys Leu Asp His Val Asn
        305                 310                 315

ATT GTT CAC TAC AAT GGC TGT TGG GAT GGA TTT GAT TAT GAT CCT GAG       1188
Ile Val His Tyr Asn Gly Cys Trp Asp Gly Phe Asp Tyr Asp Pro Glu
    320                 325                 330

ACC AGT GAT GAT TCT CTT GAG AGC AGT GAT TAT GAT CCT GAG AAC AGC       1236
Thr Ser Asp Asp Ser Leu Glu Ser Ser Asp Tyr Asp Pro Glu Asn Ser
335                 340                 345                 350

AAA AAT AGT TCA AGG TCA AAG ACT AAG TGC CTT TTC ATC CAA ATG GAA       1284
Lys Asn Ser Ser Arg Ser Lys Thr Lys Cys Leu Phe Ile Gln Met Glu
                355                 360                 365

TTC TGT GAT AAA GGG ACC TTG GAA CAA TGG ATT GAA AAA AGA AGA GGC       1332
Phe Cys Asp Lys Gly Thr Leu Glu Gln Trp Ile Glu Lys Arg Arg Gly
            370                 375                 380

GAG AAA CTA GAC AAA GTT TTG GCT TTG GAA CTC TTT GAA CAA ATA ACA       1380
Glu Lys Leu Asp Lys Val Leu Ala Leu Glu Leu Phe Glu Gln Ile Thr
        385                 390                 395

AAA GGG GTG GAT TAT ATA CAT TCA AAA AAA TTA ATT CAT AGA GAT CTT       1428
Lys Gly Val Asp Tyr Ile His Ser Lys Lys Leu Ile His Arg Asp Leu
    400                 405                 410

AAG CCA AGT AAT ATA TTC TTA GTA GAT ACA AAA CAA GTA AAG ATT GGA       1476
Lys Pro Ser Asn Ile Phe Leu Val Asp Thr Lys Gln Val Lys Ile Gly
415                 420                 425                 430

GAC TTT GGA CTT GTA ACA TCT CTG AAA AAT GAT GGA AAG CGA ACA AGG       1524
Asp Phe Gly Leu Val Thr Ser Leu Lys Asn Asp Gly Lys Arg Thr Arg
                435                 440                 445

AGT AAG GGA ACT TTG CGA TAC ATG AGC CCA GAA CAG ATT TCT TCG CAA       1572
Ser Lys Gly Thr Leu Arg Tyr Met Ser Pro Glu Gln Ile Ser Ser Gln
            450                 455                 460

GAC TAT GGA AAG GAA GTG GAC CTC TAC GCT TTG GGG CTA ATT CTT GCT      1620
 Asp Tyr Gly Lys Glu Val Asp Leu Tyr Ala Leu Gly Leu Ile Leu Ala
         465                 470                 475

GAA CTT CTT CAT GTA TGT GAC ACT GCT TTT GAA ACA TCA AAG TTT TTC       1668
Glu Leu Leu His Val Cys Asp Thr Ala Phe Glu Thr Ser Lys Phe Phe
    480                 485                 490

ACA GAC CTA CGG GAT GGC ATC ATC TCA GAT ATA TTT GAT AAA AAA GAA       1716
Thr Asp Leu Arg Asp Gly Ile Ile Ser Asp Ile Phe Asp Lys Lys Glu
495                 500                 505                 510

AAA ACT CTT CTA CAG AAA TTA CTC TCA AAG AAA CCT GAG GAT CGA CCT       1764
Lys Thr Leu Leu Gln Lys Leu Leu Ser Lys Lys Pro Glu Asp Arg Pro
                515                 520                 525

AAC ACA TCT GAA ATA CTA AGG ACC TTG ACT GTG TGG AAG AAA AGC CCA       1812
Asn Thr Ser Glu Ile Leu Arg Thr Leu Thr Val Trp Lys Lys Ser Pro
            530                 535                 540

GAG AAA AAT GAA CGA CAC ACA TGT TAGAGCCCTT CTGAAAAAGT ATCCTGCTTC      1866
Glu Lys Asn Glu Arg His Thr Cys
        545                 550
```

-continued

```
TGATATGCAG    TTTTCCTTAA    ATTATCTAAA    ATCTGCTAGG    GAATATCAAT    AGATATTTAC    1926
CTTTTATTTT    AATGTTTCCT    TTAATTTTTT    ACTATTTTA     CTAATCTTTC    TGCAGAAACA    1986
GAAAGGTTTT    CTTCTTTTTG    CTTCAAAAAC    ATTCTTACAT    TTACTTTTTC    CTGGCTCATC    2046
TCTTTATTCT    TTTTTTTTTT    TTTAAAGAC     AGAGTCTCGC    TCTGTTGCCC    AGGCTGGAGT    2106
GCAATGACAC    AGTCTTGGCT    CACTGCAACT    TCTGCCTCTT    GGGTTCAAGT    GATTCTCCTG    2166
CCTCAGCCTC    CTGAGTAGCT    GGATTACACG    CATGTGCCAC    CCACCCAACT    AATTTTTGTG    2226
TTTTAATAA     AGACAGGCTT    TCACCATGTT    GGCCAGGCTG    CTCTCAAATC    CTGACCTCAA    2286
GTAATCCACC    TGCCTCGCCG    TCCCAAAGTG    CTGGGATTAC    AGGGATGAGC    CACCGCGCCC    2346
AGCCTCATCT    CTTTGTTCTA    AAGATGGAAA    AACCACCCCC    AAATTTCTT     TTTATACTAT    2406
TAATGAATCA    ATCAATTCAT    ATCTATTTAT    TAAATTTCTA    CGGCTTTTAG    GCCAAAAAAA    2466
TGTAAGATCG    TTCTCTGCCT    CACATAGCTT    ACAAGCCAGC    TGGAGAAATA    TGGTACTCAT    2526
TAAAAAAAAA    AAAAAAGTG     ATGTACAACC    AAAAAAAAA     AAAAAAAAA     AAAAAAAAA     2586
AAAAAAAAA     AAAAAAAAA     AAAAAAAAA     AAAAAAAAA     AA                          2628
```

( 2 ) INFORMATION FOR SEQ ID NO:2:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( v i ) ORIGINAL SOURCE:
        ( C ) INDIVIDUAL ISOLATE: F1 PRIMER, FIGURE 5

( x i ) SEQUENCE DESCRIPTION: SEQ ID NO:2:

```
CAGTTCTTCC  ATCTGACT                                                                18
```

( 2 ) INFORMATION FOR SEQ ID NO:3:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( v i ) ORIGINAL SOURCE:
        ( C ) INDIVIDUAL ISOLATE: COMPLEMENTARY SEQUENCE TO R1 PRIMER,
            FIGURE 5

( x i ) SEQUENCE DESCRIPTION: SEQ ID NO:3:

```
CCTCCACATG  ATAGGAGG                                                                18
```

( 2 ) INFORMATION FOR SEQ ID NO:4:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( v i ) ORIGINAL SOURCE:
  ( C ) INDIVIDUAL ISOLATE: COMPLEMENTARY SEQUENCE TO R2 PRIMER,
    FIGURE 5

( x i ) SEQUENCE DESCRIPTION: SEQ ID NO:4:

AGGATTATCC ATGGGGAAT    19

( 2 ) INFORMATION FOR SEQ ID NO:5:

( i ) SEQUENCE CHARACTERISTICS:
    ( A ) LENGTH: 18 base pairs
    ( B ) TYPE: nucleic acid
    ( C ) STRANDEDNESS: single
    ( D ) TOPOLOGY: linear ( i i ) MOLECULE TYPE: DNA (genomic)

( v i ) ORIGINAL SOURCE:
    ( C ) INDIVIDUAL ISOLATE: COMPLEMENTARY SEQUENCE TO R3 PRIMER,
      FIGURE 5

( x i ) SEQUENCE DESCRIPTION: SEQ ID NO:5:

CAATTGGCCG CTAAACTT    18

( 2 ) INFORMATION FOR SEQ ID NO:6:

( i ) SEQUENCE CHARACTERISTICS:
    ( A ) LENGTH: 19 base pairs
    ( B ) TYPE: nucleic acid
    ( C ) STRANDEDNESS: single
    ( D ) TOPOLOGY: linear ( i i ) MOLECULE TYPE: DNA (genomic)

( i i i ) HYPOTHETICAL: NO ( v i ) ORIGINAL SOURCE:
    ( C ) INDIVIDUAL ISOLATE: COMPLEMENTARY SEQUENCE TO R4 PRIMER,
      FIGURE 5

( x i ) SEQUENCE DESCRIPTION: SEQ ID NO:6:

GATAATCTAC AGTGACAGT    19

( 2 ) INFORMATION FOR SEQ ID NO:7:

( i ) SEQUENCE CHARACTERISTICS:
    ( A ) LENGTH: 19 base pairs
    ( B ) TYPE: nucleic acid
    ( C ) STRANDEDNESS: single
    ( D ) TOPOLOGY: linear ( i i ) MOLECULE TYPE: DNA (genomic)

( i i i ) HYPOTHETICAL: NO ( v i ) ORIGINAL SOURCE:
    ( C ) INDIVIDUAL ISOLATE: COMPLEMENTARY SEQUENCE TO R5 PRIMER,
      FIGURE 5

( x i ) SEQUENCE DESCRIPTION: SEQ ID NO:7:

AGGTGGATTT GGCCAAGTT    19

( 2 ) INFORMATION FOR SEQ ID NO:8:

( i ) SEQUENCE CHARACTERISTICS:
    ( A ) LENGTH: 18 base pairs
    ( B ) TYPE: nucleic acid
    ( C ) STRANDEDNESS: single
    ( D ) TOPOLOGY: linear ( i i ) MOLECULE TYPE: DNA (genomic)

(i i i) HYPOTHETICAL: NO (v i) ORIGINAL SOURCE:
(C) INDIVIDUAL ISOLATE: COMPLEMENTARY SEQUENCE TO R6 PRIMER, FIGURE 5

(x i) SEQUENCE DESCRIPTION: SEQ ID NO:8:

ACCAGTGATG ATTCTCTT    18

(2) INFORMATION FOR SEQ ID NO:9:

(i) SEQUENCE CHARACTERISTICS:
(A) LENGTH: 18 base pairs
(B) TYPE: nucleic acid
(C) STRANDEDNESS: single
(D) TOPOLOGY: linear (i i) MOLECULE TYPE: DNA (genomic)

(i i i) HYPOTHETICAL: NO (v i) ORIGINAL SOURCE:
(C) INDIVIDUAL ISOLATE: COMPLEMENTARY SEQUENCE TO R7 PRIMER, FIGURE 5

(x i) SEQUENCE DESCRIPTION: SEQ ID NO:9:

GAACAAATAA CAAAAGGG    18

(2) INFORMATION FOR SEQ ID NO:10:

(i) SEQUENCE CHARACTERISTICS:
(A) LENGTH: 18 base pairs
(B) TYPE: nucleic acid
(C) STRANDEDNESS: single
(D) TOPOLOGY: linear (i i) MOLECULE TYPE: DNA (genomic)

(i i i) HYPOTHETICAL: NO (v i) ORIGINAL SOURCE:
(C) INDIVIDUAL ISOLATE: COMPLEMENTARY SEQUENCE TO R8 PRIMER, FIGURE 5

(x i) SEQUENCE DESCRIPTION: SEQ ID NO:10:

AGCCCAGAAC AGATTTCT    18

(2) INFORMATION FOR SEQ ID NO:11:

(i) SEQUENCE CHARACTERISTICS:
(A) LENGTH: 18 base pairs
(B) TYPE: nucleic acid
(C) STRANDEDNESS: single
(D) TOPOLOGY: linear (i i) MOLECULE TYPE: DNA (genomic)

(i i i) HYPOTHETICAL: NO (v i) ORIGINAL SOURCE:
(C) INDIVIDUAL ISOLATE: COMPLEMENTARY SEQUENCE TO R9 PRIMER, FIGURE 5

(x i) SEQUENCE DESCRIPTION: SEQ ID NO:11:

CAGAAATTAC TCTCAAAG    18

(2) INFORMATION FOR SEQ ID NO:12:

(i) SEQUENCE CHARACTERISTICS:
(A) LENGTH: 18 base pairs
(B) TYPE: nucleic acid (C) STRANDEDNESS: single
(D) TOPOLOGY: linear (ii) MOLECULE TYPE: DNA (genomic)

(iii) HYPOTHETICAL: NO (vi) ORIGINAL SOURCE:
(C) INDIVIDUAL ISOLATE: COMPLEMENTARY SEQUENCE TO R10 PRIMER, FIGURE 5

(xi) SEQUENCE DESCRIPTION: SEQ ID NO:12:

AGTTTTCCTT AAATTATC                                                18

(2) INFORMATION FOR SEQ ID NO:13:

(i) SEQUENCE CHARACTERISTICS:
(A) LENGTH: 33 base pairs
(B) TYPE: nucleic acid
(C) STRANDEDNESS: single
(D) TOPOLOGY: linear (ii) MOLECULE TYPE: DNA (genomic)

(iii) HYPOTHETICAL: NO (vi) ORIGINAL SOURCE:
(C) INDIVIDUAL ISOLATE: COMPLEMENTARY TO THE RNA PROBE FOR PR-I, FIGURE 5

(xi) SEQUENCE DESCRIPTION: SEQ ID NO:13:

ATTGGCTCAG GTGGATTTGG CCAAGTTTTC AAA                                33

(2) INFORMATION FOR SEQ ID NO:14:

(i) SEQUENCE CHARACTERISTICS:
(A) LENGTH: 15 base pairs
(B) TYPE: nucleic acid
(C) STRANDEDNESS: single
(D) TOPOLOGY: linear (ii) MOLECULE TYPE: DNA (genomic)

(iii) HYPOTHETICAL: NO (vi) ORIGINAL SOURCE:
(C) INDIVIDUAL ISOLATE: COMPLEMENTARY TO THE RNA PROBE FOR PR-II, FIGURE 5

(xi) SEQUENCE DESCRIPTION: SEQ ID NO:14:

GTTATTAAAC GTGTT                                                   15

(2) INFORMATION FOR SEQ ID NO:15:

(i) SEQUENCE CHARACTERISTICS:
(A) LENGTH: 21 base pairs
(B) TYPE: nucleic acid
(C) STRANDEDNESS: single
(D) TOPOLOGY: linear (ii) MOLECULE TYPE: DNA (genomic)

(iii) HYPOTHETICAL: NO (vi) ORIGINAL SOURCE:
(C) INDIVIDUAL ISOLATE: COMPLEMENTARY TO THE RNA PROBE FOR PR-III, FIGURE 5

(xi) SEQUENCE DESCRIPTION: SEQ ID NO:15:

GCGGAGCGTG AAGTAAAAGC A                                            21

(2) INFORMATION FOR SEQ ID NO:16:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( i i ) MOLECULE TYPE: DNA (genomic)

( i i i ) HYPOTHETICAL: NO ( v i ) ORIGINAL SOURCE:
    ( C ) INDIVIDUAL ISOLATE: COMPLEMENTARY TO THE RNA PROBE FOR PR-IV, FIGURE 5

( x i ) SEQUENCE DESCRIPTION: SEQ ID NO:16:

```
CATGTAAATA TTGTT                                                          15
```

( 2 ) INFORMATION FOR SEQ ID NO:17:

( i ) SEQUENCE CHARACTERISTICS:
    ( A ) LENGTH: 33 base pairs
    ( B ) TYPE: nucleic acid
    ( C ) STRANDEDNESS: single
    ( D ) TOPOLOGY: linear ( i i ) MOLECULE TYPE: DNA (genomic)

( i i i ) HYPOTHETICAL: NO ( v i ) ORIGINAL SOURCE:
    ( C ) INDIVIDUAL ISOLATE: COMPLEMENTARY TO THE RNA PROBE FOR PR-V, FIGURE 5

( x i ) SEQUENCE DESCRIPTION: SEQ ID NO:17:

```
GATTATGATC CTGAGACCAG TGATGATTCT CTT                                      33
```

( 2 ) INFORMATION FOR SEQ ID NO:18:

( i ) SEQUENCE CHARACTERISTICS:
    ( A ) LENGTH: 60 base pairs
    ( B ) TYPE: nucleic acid
    ( C ) STRANDEDNESS: single
    ( D ) TOPOLOGY: linear ( i i ) MOLECULE TYPE: DNA (genomic)

( i i i ) HYPOTHETICAL: NO ( v i ) ORIGINAL SOURCE:
    ( C ) INDIVIDUAL ISOLATE: COMPLEMENTARY TO THE RNA PROBE FOR PR-VI, FIGURE 5

( x i ) SEQUENCE DESCRIPTION: SEQ ID NO:18:

```
GGGGTGGATT ATATACATTC AAAAAAATTA ATTCATAGAG ATCTTAAGCC AAGTAATATA         60
```

( 2 ) INFORMATION FOR SEQ ID NO:19:

( i ) SEQUENCE CHARACTERISTICS:
    ( A ) LENGTH: 18 base pairs
    ( B ) TYPE: nucleic acid
    ( C ) STRANDEDNESS: single
    ( D ) TOPOLOGY: linear ( i i ) MOLECULE TYPE: DNA (genomic)

( i i i ) HYPOTHETICAL: NO ( v i ) ORIGINAL SOURCE:
    ( C ) INDIVIDUAL ISOLATE: COMPLEMENTARY TO THE RNA PROBE FOR PR-VII, FIGURE 5

( x i ) SEQUENCE DESCRIPTION: SEQ ID NO:19:

ATTGGAGACT TTGGACTT 18

(2) INFORMATION FOR SEQ ID NO:20:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (vi) ORIGINAL SOURCE:
        (C) INDIVIDUAL ISOLATE: COMPLEMENTARY TO THE RNA PROBE FOR
            PR-VIII, FIGURE 5

(xi) SEQUENCE DESCRIPTION: SEQ ID NO:20:

GGAACTTTGC GATACATGAG CCCAGAA 27

(2) INFORMATION FOR SEQ ID NO:21:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (vi) ORIGINAL SOURCE:
        (C) INDIVIDUAL ISOLATE: COMPLEMENTARY TO THE RNA PROBE FOR
            PR-IX, FIGURE 5

(xi) SEQUENCE DESCRIPTION: SEQ ID NO:21:

GACCTCTACG CTTTGGGGCT AATTCTTGCT 30

(2) INFORMATION FOR SEQ ID NO:22:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (vi) ORIGINAL SOURCE:
        (C) INDIVIDUAL ISOLATE: COMPLEMENTARY TO THE RNA PROBE FOR
            PR-X, FIGURE 5

(xi) SEQUENCE DESCRIPTION: SEQ ID NO:22:

GACCTACGGG ATGGCATCAT CTCAGATATA 30

(2) INFORMATION FOR SEQ ID NO:23:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (vi) ORIGINAL SOURCE:
        (C) INDIVIDUAL ISOLATE: COMPLEMENTARY TO THE RNA PROBE FOR

PR-XI, FIGURE 5

( x i ) SEQUENCE DESCRIPTION: SEQ ID NO:23:

CTACAGAAAT TACTCTCAAA GAAACCTGAG GATCGA  36

( 2 ) INFORMATION FOR SEQ ID NO:24:

( i ) SEQUENCE CHARACTERISTICS:
      ( A ) LENGTH: 18 base pairs
      ( B ) TYPE: nucleic acid
      ( C ) STRANDEDNESS: single
      ( D ) TOPOLOGY: linear ( i i ) MOLECULE TYPE: DNA (genomic)

( i i i ) HYPOTHETICAL: NO ( v i ) ORIGINAL SOURCE:
      ( C ) INDIVIDUAL ISOLATE: COMPLEMENTARY TO THE RNA PROBE FOR
          PR-XII (VA), FIGURE 5

( x i ) SEQUENCE DESCRIPTION: SEQ ID NO:24:

CTTTTCATCC AAATGGAA  18

( 2 ) INFORMATION FOR SEQ ID NO:25:

( i ) SEQUENCE CHARACTERISTICS:
      ( A ) LENGTH: 550 amino acids
      ( B ) TYPE: amino acid
      ( D ) TOPOLOGY: linear ( i i ) MOLECULE TYPE: protein ( x i ) SEQUENCE DESCRIPTION: SEQ ID NO:25:

| Met | Ala | Gly | Asp | Leu | Ser | Ala | Gly | Phe | Phe | Met | Glu | Glu | Leu | Asn | Thr |
|---|---|---|---|---|---|---|---|---|---|---|---|---|---|---|---|
| 1 |   |   |   | 5 |   |   |   |   | 10 |   |   |   |   | 15 |   |

| Tyr | Arg | Gln | Lys | Gln | Gly | Val | Val | Leu | Lys | Tyr | Gln | Glu | Leu | Pro | Asn |
|---|---|---|---|---|---|---|---|---|---|---|---|---|---|---|---|
|   |   |   | 20 |   |   |   |   | 25 |   |   |   |   | 30 |   |   |

| Ser | Gly | Pro | Pro | His | Asp | Arg | Arg | Phe | Thr | Phe | Gln | Val | Ile | Ile | Asp |
|---|---|---|---|---|---|---|---|---|---|---|---|---|---|---|---|
|   |   | 35 |   |   |   |   | 40 |   |   |   |   | 45 |   |   |   |

| Gly | Arg | Glu | Phe | Pro | Glu | Gly | Glu | Gly | Arg | Ser | Lys | Lys | Glu | Ala | Lys |
|---|---|---|---|---|---|---|---|---|---|---|---|---|---|---|---|
|   | 50 |   |   |   |   | 55 |   |   |   |   | 60 |   |   |   |   |

| Asn | Ala | Ala | Ala | Lys | Leu | Ala | Val | Glu | Ile | Leu | Asn | Lys | Glu | Lys | Lys |
|---|---|---|---|---|---|---|---|---|---|---|---|---|---|---|---|
| 65 |   |   |   |   | 70 |   |   |   |   | 75 |   |   |   |   | 80 |

| Ala | Val | Ser | Pro | Leu | Leu | Leu | Thr | Thr | Thr | Asn | Ser | Ser | Glu | Gly | Leu |
|---|---|---|---|---|---|---|---|---|---|---|---|---|---|---|---|
|   |   |   |   | 85 |   |   |   |   | 90 |   |   |   |   | 95 |   |

| Ser | Met | Gly | Asn | Tyr | Ile | Gly | Leu | Ile | Asn | Arg | Ile | Ala | Gln | Lys | Lys |
|---|---|---|---|---|---|---|---|---|---|---|---|---|---|---|---|
|   |   |   | 100 |   |   |   |   | 105 |   |   |   |   | 110 |   |   |

| Arg | Leu | Thr | Val | Asn | Tyr | Glu | Gln | Cys | Ala | Ser | Gly | Val | His | Gly | Pro |
|---|---|---|---|---|---|---|---|---|---|---|---|---|---|---|---|
|   |   | 115 |   |   |   |   | 120 |   |   |   |   | 125 |   |   |   |

| Glu | Gly | Phe | His | Tyr | Lys | Cys | Lys | Met | Gly | Gln | Lys | Glu | Tyr | Ser | Ile |
|---|---|---|---|---|---|---|---|---|---|---|---|---|---|---|---|
|   | 130 |   |   |   |   | 135 |   |   |   |   | 140 |   |   |   |   |

| Gly | Thr | Gly | Ser | Thr | Lys | Gln | Glu | Ala | Lys | Gln | Leu | Ala | Ala | Lys | Leu |
|---|---|---|---|---|---|---|---|---|---|---|---|---|---|---|---|
| 145 |   |   |   |   | 150 |   |   |   |   | 155 |   |   |   |   | 160 |

| Ala | Tyr | Leu | Gln | Ile | Leu | Ser | Glu | Glu | Thr | Ser | Val | Lys | Ser | Asp | Tyr |
|---|---|---|---|---|---|---|---|---|---|---|---|---|---|---|---|
|   |   |   |   | 165 |   |   |   |   | 170 |   |   |   |   | 175 |   |

| Leu | Ser | Ser | Gly | Ser | Phe | Ala | Thr | Thr | Cys | Glu | Ser | Gln | Ser | Asn | Ser |
|---|---|---|---|---|---|---|---|---|---|---|---|---|---|---|---|
|   |   |   | 180 |   |   |   |   | 185 |   |   |   |   | 190 |   |   |

| Leu | Val | Thr | Ser | Thr | Leu | Ala | Ser | Glu | Ser | Ser | Ser | Glu | Gly | Asp | Phe |
|---|---|---|---|---|---|---|---|---|---|---|---|---|---|---|---|
|   |   | 195 |   |   |   |   | 200 |   |   |   |   | 205 |   |   |   |

| Ser | Ala | Asp | Thr | Ser | Glu | Ile | Ile | Tyr | Ser | Asp | Ser | Leu | Asn | Ser | Ser |
|---|---|---|---|---|---|---|---|---|---|---|---|---|---|---|---|
|   | 210 |   |   |   |   | 215 |   |   |   |   | 220 |   |   |   |   |

| Ser | Leu | Leu | Met | Asn | Gly | Leu | Arg | Asn | Asn | Gln | Arg | Lys | Ala | Lys | Arg |
| 225 | | | | | 230 | | | | | 235 | | | | | 240 |

| Ser | Leu | Ala | Pro | Arg | Phe | Asp | Leu | Pro | Asp | Met | Lys | Glu | Thr | Lys | Tyr |
| | | | | 245 | | | | | 250 | | | | | 255 | |

| Thr | Val | Asp | Lys | Arg | Phe | Gly | Met | Asp | Phe | Lys | Glu | Ile | Glu | Leu | Ile |
| | | | | 260 | | | | | 265 | | | | | 270 | |

| Gly | Ser | Gly | Gly | Phe | Gly | Gln | Val | Phe | Lys | Ala | Lys | His | Arg | Ile | Asp |
| | | | 275 | | | | | 280 | | | | | 285 | | |

| Gly | Lys | Thr | Tyr | Val | Ile | Lys | Arg | Val | Lys | Tyr | Asn | Asn | Glu | Lys | Ala |
| | 290 | | | | | 295 | | | | | 300 | | | | |

| Glu | Arg | Glu | Val | Lys | Ala | Leu | Ala | Lys | Leu | Asp | His | Val | Asn | Ile | Val |
| 305 | | | | | 310 | | | | | 315 | | | | | 320 |

| His | Tyr | Asn | Gly | Cys | Trp | Asp | Gly | Phe | Asp | Tyr | Asp | Pro | Glu | Thr | Ser |
| | | | | 325 | | | | | 330 | | | | | 335 | |

| Asp | Asp | Ser | Leu | Glu | Ser | Ser | Asp | Tyr | Asp | Pro | Glu | Asn | Ser | Lys | Asn |
| | | | 340 | | | | | 345 | | | | | 350 | | |

| Ser | Ser | Arg | Ser | Lys | Thr | Lys | Cys | Leu | Phe | Ile | Gln | Met | Glu | Phe | Cys |
| | | 355 | | | | | 360 | | | | | 365 | | | |

| Asp | Lys | Gly | Thr | Leu | Glu | Gln | Trp | Ile | Glu | Lys | Arg | Arg | Gly | Glu | Lys |
| | 370 | | | | | 375 | | | | | 380 | | | | |

| Leu | Asp | Lys | Val | Leu | Ala | Leu | Glu | Leu | Phe | Glu | Gln | Ile | Thr | Lys | Gly |
| 385 | | | | | 390 | | | | | 395 | | | | | 400 |

| Val | Asp | Tyr | Ile | His | Ser | Lys | Lys | Leu | Ile | His | Arg | Asp | Leu | Lys | Pro |
| | | | | 405 | | | | | 410 | | | | | 415 | |

| Ser | Asn | Ile | Phe | Leu | Val | Asp | Thr | Lys | Gln | Val | Lys | Ile | Gly | Asp | Phe |
| | | | 420 | | | | | 425 | | | | | 430 | | |

| Gly | Leu | Val | Thr | Ser | Leu | Lys | Asn | Asp | Gly | Lys | Arg | Thr | Arg | Ser | Lys |
| | | 435 | | | | | 440 | | | | | 445 | | | |

| Gly | Thr | Leu | Arg | Tyr | Met | Ser | Pro | Glu | Gln | Ile | Ser | Ser | Gln | Asp | Tyr |
| | 450 | | | | | 455 | | | | | 460 | | | | |

| Gly | Lys | Glu | Val | Asp | Leu | Tyr | Ala | Leu | Gly | Leu | Ile | Leu | Ala | Glu | Leu |
| 465 | | | | | 470 | | | | | 475 | | | | | 480 |

| Leu | His | Val | Cys | Asp | Thr | Ala | Phe | Glu | Thr | Ser | Lys | Phe | Phe | Thr | Asp |
| | | | | 485 | | | | | 490 | | | | | 495 | |

| Leu | Arg | Asp | Gly | Ile | Ile | Ser | Asp | Ile | Phe | Asp | Lys | Lys | Glu | Lys | Thr |
| | | | 500 | | | | | 505 | | | | | 510 | | |

| Leu | Leu | Gln | Lys | Leu | Leu | Ser | Lys | Lys | Pro | Glu | Asp | Arg | Pro | Asn | Thr |
| | | 515 | | | | | 520 | | | | | 525 | | | |

| Ser | Glu | Ile | Leu | Arg | Thr | Leu | Thr | Val | Trp | Lys | Lys | Ser | Pro | Glu | Lys |
| | 530 | | | | | 535 | | | | | 540 | | | | |

| Asn | Glu | Arg | His | Thr | Cys |
| 545 | | | | | 550 |

( 2 ) INFORMATION FOR SEQ ID NO: 26:

( i ) SEQUENCE CHARACTERISTICS:
        ( A ) LENGTH: 1687 base pairs
        ( B ) TYPE: nucleic acid
        ( C ) STRANDEDNESS: double
        ( D ) TOPOLOGY: linear ( i i ) MOLECULE TYPE: cDNA to mRNA ( i i i ) HYPOTHETICAL: NO ( v i ) ORIGINAL SOURCE:
        ( C ) INDIVIDUAL ISOLATE: BOVINE P58 GENE, FIGURE 10A ( x i ) SEQUENCE DESCRIPTION: SEQ ID NO: 26:

| | | | | | | | | | | | | | | | | |
|---|---|---|---|---|---|---|---|---|---|---|---|---|---|---|---|---|
| CGGCCCGAGC | GAGAGCAGAC | TGCGGGCGCC | CGGCCGCAGC | TGCAGCCTGA | GCGCCGCGGC | | | | | | | | | | | 60 |
| GGGGGGCTGG | TGGGCCCCGC | AGCTTTGCTC | CTCCTCTGCG | CCCGCGCTCT | CGGAC | | | | | | | | | | | 115 |

| ATG | GTG | GCC | CCC | GGC | TCT | GTG | ACC | AGC | CGG | CTG | GGC | TCG | GTG | TTC | CCT | 163 |
|---|---|---|---|---|---|---|---|---|---|---|---|---|---|---|---|---|
| Met | Val | Ala | Pro | Gly | Ser | Val | Thr | Ser | Arg | Leu | Gly | Ser | Val | Phe | Pro | |
| 1 | | | | 5 | | | | | 10 | | | | | 15 | | |

| TTC | CTG | CTG | GTC | CTG | GTG | GAC | CTG | CAG | TAC | GAA | GGT | GCT | GAA | TGT | GGA | 211 |
|---|---|---|---|---|---|---|---|---|---|---|---|---|---|---|---|---|
| Phe | Leu | Leu | Val | Leu | Val | Asp | Leu | Gln | Tyr | Glu | Gly | Ala | Glu | Cys | Gly | |
| | | | | 20 | | | | | 25 | | | | | 30 | | |

| GTA | AAT | GCA | GAT | GTT | GAG | AAG | CAT | CTG | GAA | TTG | GGC | AAG | AAG | CTG | CTC | 259 |
|---|---|---|---|---|---|---|---|---|---|---|---|---|---|---|---|---|
| Val | Asn | Ala | Asp | Val | Glu | Lys | His | Leu | Glu | Leu | Gly | Lys | Lys | Leu | Leu | |
| | | 35 | | | | | 40 | | | | | 45 | | | | |

| GCA | GCC | GGA | CAG | CTC | GCG | GAT | GCG | TTA | TCT | CAG | TTT | CAC | GCT | GCA | GTA | 307 |
|---|---|---|---|---|---|---|---|---|---|---|---|---|---|---|---|---|
| Ala | Ala | Gly | Gln | Leu | Ala | Asp | Ala | Leu | Ser | Gln | Phe | His | Ala | Ala | Val | |
| | | 50 | | | | | 55 | | | | | 60 | | | | |

| GAT | GGT | GAC | CCT | GAT | AAC | TAT | ATT | GCT | TAC | TAT | CGG | AGA | GCT | ACT | GTC | 355 |
|---|---|---|---|---|---|---|---|---|---|---|---|---|---|---|---|---|
| Asp | Gly | Asp | Pro | Asp | Asn | Tyr | Ile | Ala | Tyr | Tyr | Arg | Arg | Ala | Thr | Val | |
| 65 | | | | | 70 | | | | | 75 | | | | | 80 | |

| TTT | TTA | GCT | ATG | GGC | AAA | TCA | AAA | GCA | GCA | CTT | CCT | GAT | TTA | ACT | AAA | 403 |
|---|---|---|---|---|---|---|---|---|---|---|---|---|---|---|---|---|
| Phe | Leu | Ala | His | Gly | Lys | Ser | Lys | Ala | Ala | Leu | Pro | Asp | Leu | Thr | Lys | |
| | | | | 85 | | | | | 90 | | | | | 95 | | |

| GTG | ATT | GAA | TTG | AAG | ATG | GAT | TTC | ACT | GCA | GCA | AGA | TTA | CAG | AGA | GGT | 451 |
|---|---|---|---|---|---|---|---|---|---|---|---|---|---|---|---|---|
| Val | Ile | Glu | Leu | Lys | Met | Asp | Phe | Thr | Ala | Ala | Arg | Leu | Gln | Arg | Gly | |
| | | | | 100 | | | | | 105 | | | | | 110 | | |

| CAC | TTA | TTA | CTC | AAA | CAA | GGA | AAA | CTT | GAT | GAA | GCA | GAA | GAT | GAT | TTT | 499 |
|---|---|---|---|---|---|---|---|---|---|---|---|---|---|---|---|---|
| His | Leu | Leu | Leu | Lys | Gln | Gly | Lys | Leu | Asp | Glu | Ala | Glu | Asp | Asp | Phe | |
| | | 115 | | | | | 120 | | | | | 125 | | | | |

| AAA | AAA | GTG | CTC | AAG | TCA | AAT | CCA | AGT | GAA | AAT | GAA | GAG | AAG | GAG | GCC | 547 |
|---|---|---|---|---|---|---|---|---|---|---|---|---|---|---|---|---|
| Lys | Lys | Val | Leu | Lys | Ser | Asn | Pro | Ser | Glu | Asn | Glu | Glu | Lys | Glu | Ala | |
| | 130 | | | | | 135 | | | | | 140 | | | | | |

| CAG | TCC | CAG | CTT | GTC | AAA | TCT | GAT | GAA | ATG | CAG | CGT | CTG | CGC | TCA | CAA | 595 |
|---|---|---|---|---|---|---|---|---|---|---|---|---|---|---|---|---|
| Gln | Ser | Gln | Leu | Val | Lys | Ser | Asp | Glu | Met | Gln | Arg | Leu | Arg | Ser | Gln | |
| 145 | | | | | 150 | | | | | 155 | | | | | 160 | |

| GCA | CTG | GAT | GCC | TTT | GAG | AGC | TCA | GAT | TTT | ACT | GCT | GCT | ATA | ACC | TTC | 643 |
|---|---|---|---|---|---|---|---|---|---|---|---|---|---|---|---|---|
| Ala | Leu | Asp | Ala | Phe | Glu | Ser | Ser | Asp | Phe | Thr | Ala | Ala | Ile | Thr | Phe | |
| | | | | 165 | | | | | 170 | | | | | 175 | | |

| CTT | GAT | AAG | ATT | TTA | GAG | GTT | TGT | GTT | TGG | GAT | GCA | GAA | CTT | CGA | GAA | 691 |
|---|---|---|---|---|---|---|---|---|---|---|---|---|---|---|---|---|
| Leu | Asp | Lys | Ile | Leu | Glu | Val | Cys | Val | Trp | Asp | Ala | Glu | Leu | Arg | Glu | |
| | | | | 180 | | | | | 185 | | | | | 190 | | |

| CTT | CGA | GCT | GAA | TGT | TTT | ATA | AAA | GAA | GGG | GAA | CCT | AGG | AAA | GCG | ATA | 739 |
|---|---|---|---|---|---|---|---|---|---|---|---|---|---|---|---|---|
| Leu | Arg | Ala | Glu | Cys | Phe | Ile | Lys | Glu | Gly | Glu | Pro | Arg | Lys | Ala | Ile | |
| | | 195 | | | | | 200 | | | | | 205 | | | | |

| AGT | GAC | TTA | AAA | GCT | TCA | TCA | AAA | TTG | AAA | AAC | GAT | AAT | ACT | GAG | GCA | 787 |
|---|---|---|---|---|---|---|---|---|---|---|---|---|---|---|---|---|
| Ser | Asp | Leu | Lys | Ala | Ser | Ser | Lys | Leu | Lys | Asn | Asp | Asn | Thr | Glu | Ala | |
| | 210 | | | | | 215 | | | | | 220 | | | | | |

| TTT | TAT | AAA | ATC | AGC | ACA | CTC | TAC | TAT | GAA | CTA | GGA | GAC | CAT | GAA | CTG | 835 |
|---|---|---|---|---|---|---|---|---|---|---|---|---|---|---|---|---|
| Phe | Tyr | Lys | Ile | Ser | Thr | Leu | Tyr | Tyr | Glu | Leu | Gly | Asp | His | Glu | Leu | |
| 225 | | | | | 230 | | | | | 235 | | | | | 240 | |

| TCT | CTC | AGT | GAA | GTT | CGT | GAA | TGT | CTT | AAA | CTT | GAC | CAG | GAT | CAT | AAA | 883 |
|---|---|---|---|---|---|---|---|---|---|---|---|---|---|---|---|---|
| Ser | Leu | Ser | Glu | Val | Arg | Glu | Cys | Leu | Lys | Leu | Asp | Gln | Asp | His | Lys | |
| | | | | 245 | | | | | 250 | | | | | 255 | | |

| AGG | TGT | TTT | GCA | CAC | TAT | AAA | CAA | GTA | AAG | AAA | CTG | AAT | AAG | CTG | ATT | 931 |
|---|---|---|---|---|---|---|---|---|---|---|---|---|---|---|---|---|
| Arg | Cys | Phe | Ala | His | Tyr | Lys | Gln | Val | Lys | Lys | Leu | Asn | Lys | Leu | Ile | |
| | | | | 260 | | | | | 265 | | | | | 270 | | |

| GAG | TCA | GCT | GAA | GAG | CTC | ATC | AAA | GAA | GGC | AGG | TAC | ACA | GAT | GCA | ATC | 979 |
|---|---|---|---|---|---|---|---|---|---|---|---|---|---|---|---|---|
| Glu | Ser | Ala | Glu | Glu | Leu | Ile | Lys | Glu | Gly | Arg | Tyr | Thr | Asp | Ala | Ile | |
| | | 275 | | | | | 280 | | | | | 285 | | | | |

| AGC | AAA | TAT | GAA | TCT | GTC | ATG | AAA | ACA | GAG | CCA | GGT | GTT | CAT | GAA | TAT | 1027 |
|---|---|---|---|---|---|---|---|---|---|---|---|---|---|---|---|---|
| Ser | Lys | Tyr | Glu | Ser | Val | Met | Lys | Thr | Glu | Pro | Gly | Val | His | Glu | Tyr | |

|   |   |   |   |   | 290 |   |   |   |   | 295 |   |   |   |   | 300 |   |   |   |   |      |
|---|---|---|---|---|-----|---|---|---|---|-----|---|---|---|---|-----|---|---|---|---|------|
| ACA | ATT | CGT | TCA | AAA | GAA | AGG | ATT | TGC | CAC | TGC | TTT | TCT | AAG | GAT | GAG |   |   |   |   | 1075 |
| Thr | Ile | Arg | Ser | Lys | Glu | Arg | Ile | Cys | His | Cys | Phe | Ser | Lys | Asp | Glu |   |   |   |   |      |
| 305 |   |   |   |   | 310 |   |   |   |   | 315 |   |   |   |   | 320 |   |   |   |   |      |

```
ACA ATT CGT TCA AAA GAA AGG ATT TGC CAC TGC TTT TCT AAG GAT GAG            1075
Thr Ile Arg Ser Lys Glu Arg Ile Cys His Cys Phe Ser Lys Asp Glu
305             310             315             320

AAG CCT GTT GAA GCT ATT CGA GTA TGT TCA GAA GTT TTA CAG GTG GAA            1123
Lys Pro Val Glu Ala Ile Arg Val Cys Ser Glu Val Leu Gln Val Glu
                325             330             335

CCT GAC AAC GTG AAT GCT CTG AAA GAC CGA GCA GAG GCC TAT TTA ATA            1171
Pro Asp Asn Val Asn Ala Leu Lys Asp Arg Ala Glu Ala Tyr Leu Ile
            340             345             350

GAA GAA ATG TAT GAT GAA GCT ATT CAG GAT TAT GAA ACT GCT CAG GAA            1219
Glu Glu Met Tyr Asp Glu Ala Ile Gln Asp Tyr Glu Thr Ala Gln Glu
        355             360             365

CAC AAT GAG AAT GAT CAG CAG ATT CGA GAA GGT CTG GAG AAA GCA CAG            1267
His Asn Glu Asn Asp Gln Gln Ile Arg Glu Gly Leu Glu Lys Ala Gln
370             375             380

AGG CTA CTG AAA CAG TCA CAG AGA CGA GAT TAT TAC AAA ATC TTG GGA            1315
Arg Leu Leu Lys Gln Ser Gln Arg Arg Asp Tyr Tyr Lys Ile Leu Gly
385             390             395             400

GTA AAA AGA AAT GCC AAA AAG CAA GAA ATC ATT AAA GCA TAC CGA AAA            1363
Val Lys Arg Asn Ala Lys Lys Gln Glu Ile Ile Lys Ala Tyr Arg Lys
                405             410             415

TTA GCA CTG CAG TGG CAC CCA GAC AAC TTC CAG AAC GAA GAA GAA AAG            1411
Leu Ala Leu Gln Trp His Pro Asp Asn Phe Gln Asn Glu Glu Glu Lys
            420             425             430

AAA AAA GCT GAG AAG AAG TTC ATT GAC ATA GCA GCT GCT AAA GAA GTC            1459
Lys Lys Ala Glu Lys Lys Phe Ile Asp Ile Ala Ala Ala Lys Glu Val
        435             440             445

CTC TCC GAT CCA GAA ATG AGG AAG AAG TTT GAT GAC GGA GAA GAC CCC            1507
Leu Ser Asp Pro Glu Met Arg Lys Lys Phe Asp Asp Gly Glu Asp Pro
450             455             460

CTG GAC GCA GAG AGC CAA CAA GGA GGT GGC AAC CCT TTC CAC AGG                1555
Leu Asp Ala Glu Ser Gln Gln Gly Gly Gly Asn Pro Phe His Arg
465             470             475             480

AGC TGG AAC TCA TGG CAA GGG TTC AGT CCC TTT AGC TCA GGC GGA CCT            1603
Ser Trp Asn Ser Trp Gln Gly Phe Ser Pro Phe Ser Ser Gly Gly Pro
                485             490             495

TTT AGA TTT AAA TTC CAC TTC AAT TAA                                        1630
Phe Arg Phe Lys Phe His Phe Asn
            500             504

ACCAGCTGTT TTTCTGCAGA AAAAAAAAAA AAAAAAAAAA AAAAAAAAAA AAAAAA              1687
```

( 2 ) INFORMATION FOR SEQ ID NO:27:

( i ) SEQUENCE CHARACTERISTICS:
        ( A ) LENGTH: 1599
        ( B ) TYPE: nucleic acid
        ( C ) STRANDEDNESS: double
        ( D ) TOPOLOGY: linear ( i i ) MOLECULE TYPE: cDNA to mRNA ( i i i ) HYPOTHETICAL: NO ( v i ) ORIGINAL SOURCE:
        ( C ) INDIVIDUAL ISOLATE: 3'UNTRANSLATED REGION OF BOVINE P58
        GENE, FIGURE 10B ( x i ) SEQUENCE DESCRIPTION: SEQ ID NO:27:

```
ACCAGCTGTT TTTCTGCTCC TCTTCCTTCA TTTTTTAAAG TTTAAAACA  AACAAAATAA     60

CCTTGTTCCG GGATCCTATT GAAAAAGAAA ATTCAAATCT TTCAGTTTGT CCACGACCAA   120

AGAGGTGTTC AGAATGGCAG TGTCTGTTCT TATTCATTGC AGACTTGAGG CTGATGGGGG   180
```

| | | | | | | |
|---|---|---|---|---|---|---|
| TGAGGGCAGG | GAGGCAGGTG | GGCTTCTGTT | TCTGGCAGAG | CAGCCTGTGT | CTGTGCTGTG | 240 |
| ACCGGATGGA | AGCAGCAGTC | TGAGGCAGGT | GCACAGATCT | TTTATCTTCT | ACACTGGAGC | 300 |
| AGGTGAGATT | CTCTTCTTGT | TGCATACGTG | TCAGCACCTG | CGTGTGTGAG | GAGGAGCCTG | 360 |
| GGCTGTCAGC | ATTCTCCAAG | AGGAATGACC | CTTCTGAGCT | GTATGTTCTT | AGGCACAACT | 420 |
| TGGCTTCGAC | TCTGGTCTGT | CCGGTCACCT | GTCACTATGT | TCTTAGGCAC | AACTTGGCTT | 480 |
| CGACTCTGGT | CTGTCCGGTC | ACCTGTCACT | ATGTTACATT | TCCACTTGCG | TTCCCATCTC | 540 |
| TTGCTGAGCA | TGAACGTGGC | TGCTGTTGAA | GGTGGCAGAG | CCCTTAGAGA | ACCTGCTACG | 600 |
| AATGGCAGGG | TGAGGTCTGG | TAAATACGTA | TTTTTTTGT | TCAGTACCTG | AAGGAGAATA | 660 |
| CTGAAAACAA | TATTAAATAC | AATGAACTAA | AAATATGTAA | AATAAGTTCA | GATAACATAG | 720 |
| CAGTGGTATT | TAAATAATAT | TGCTGTAGTA | CAGAATTAAC | AACTGAAGTT | GTGAGTTGTT | 780 |
| ACAGCATTTC | CTGTGGCAGG | ATTGGCTTAG | AATGTAAAGT | TGCTCAGTCA | ACATAGACAG | 840 |
| TATGCCATGT | CTCCCACTTT | TGGTAAGTTC | AGCAGCTTCT | CTTACGTCCT | GGCCTCCCTG | 900 |
| GCCCGTGGGT | GCCCACGTGG | GACTGCTTTG | AGGTGGGTGT | TAAGTAGCAG | GCCTCCCCTT | 960 |
| TACAGACCTT | GATGCCTCTG | GAAGTTCTGC | CAGGAAAGAA | ACAGGTTTAC | AGACCTAGTG | 1020 |
| AGCTCTGGCT | GTATGTCCAC | TATCAAGATA | GCATCTCTTT | TTGGGATACC | TTCTTACCTT | 1080 |
| TTAAGAAAAA | TGAAACTATT | CAGTCTTTAT | ATGCTGGATA | ATTTTTTCCT | TAAAAGAAAA | 1140 |
| ATAAGTGTTA | ATCTATAACA | TTAAATATTT | ATGGATAGGG | ATTCCATAAA | ATATTATGGA | 1200 |
| ACTATTGATG | CTGCATTTAA | AATCTAAGAA | TTATTTAGAT | AAAAATTATT | ACCTTTATTC | 1260 |
| TAGAAAGGTT | TTGTGTTTTT | TTTTGCCTC | AGAACATTTT | GACAATTTAA | GTAGGATGGG | 1320 |
| CCTAATATAC | TGACTGCTTT | TTGGGAAATC | AAGCATCTTC | TGAGTTGTTG | GGGCTGTCCT | 1380 |
| ACCACTAATA | TCCACAACCA | GCCAGCCAAG | CACAAATAGT | TTCCTTCTAC | AGTCATTCTG | 1440 |
| AAACATACTT | GGAAAAGTTT | TTTAATCTGA | GGGACAAAAA | CAAAATAGTT | GAGTTGGACA | 1500 |
| CAACACGTTA | AATGCTTTTT | GCATCTATTT | AGAAGTTTAT | TTCTTTCCAA | TAAACAAGAT | 1560 |
| GGCATTTTGA | AAACTAAAAA | AAAAAAAAAA | AAAAAAAAA | | | 1599 |

ANTI-TUMOR AGENT ASSAY USING PKR

CROSS REFERENCE TO RELATED APPLICATIONS

This application is a continuation-in-part of application Ser. No. 08/141,244, titled "Tumor-Cell Assay and Therapy," filed Oct. 22, 1993, by Sonenberg, et al., now abandoned, which is a continuation-in-part of application Ser. No. 07/953,681, titled "Tumor-cell Assay Method and Kit," filed Sep. 29, 1992 by Sonenberg et al., now abandoned; the disclosures of which are incorporated herein by reference.

This invention was made with government support under grant numbers AI22646 & RR00166 awarded by the National Institutes of Health. The government has certain rights in the invention.

FIELD OF THE INVENTION

This invention relates to methods for detecting neoplastic cells and preventing and treating neoplasm. This invention also relates to methods for screening for anti-tumor agents, the novel agents identified using such screening methods, and their use as anti-tumor agents.

BACKGROUND OF THE INVENTION

A variety of histological and biochemical tests are currently used for diagnosing the presence of human cancers. For a variety of solid tumors, tissue biopsies from the region of interest are examined histologically, for staining and morphological patterns which are characteristic of neoplastic cells. Specific types of white blood cells can be similarly examined for characteristic morphological and staining patterns. Rate of cell growth in soft agar is another feature of biopsies or blood cells which can be used to identify neoplastic cells.

A variety of tumor types can be identified by tumor-specific surface antigens, which allow detection by antibody binding to the cells. Similarly, some cancers can be identified immunologically by the presence of tumor-specific serum markers.

Another detection method involves detection of genomic mutation, e.g., by restriction fragment-length polymorphisms (RFLPs). Certain leukemias, for example, are characterized by a chromosomal rearrangement that yields a distinctive RFLP pattern.

It is often advantageous, in screening human tissue or blood cells for neoplastic-cell characteristics, to identify the biochemical mutation or lesion which may be responsible for the neoplastic state of the cells. The biochemical lesion may indicate, for example, the stage of development of the neoplasm, the prognosis for treatment, and the best treatment modalities.

SUMMARY OF THE INVENTION

The present invention features methods for screening human tissue for the presence of neoplastic cells, based on measuring the activities of PKR (double-stranded RNA-activated protein kinase), P58 protein, and anti-P58 protein. These methods identify neoplastic cells on the basis of below-normal PKR activity, abnormal P58 activity, abnormal anti-P58 activity, or any combination of the three activities.

The present invention also features methods for screening for anti-tumor agents and for using these agents to prevent and treat neoplasm. These methods identify anti-tumor agents that either increase PKR and/or anti-P58 activities or decrease P58 activity. Once isolated, the anti-tumor agents can be formulated in therapeutic products (or even prophylactic products) in pharmaceutically acceptable formulations, and used for prevention and/or treatment of neoplasm.

Thus, in a first aspect, this invention features methods for screening for neoplastic cells by assaying PKR expression, activity, or mutation.

In one general embodiment, PKR activity is determined directly by measuring the protein kinase activity of PKR in cell extract from test cells to be screened. The kinase activity may be measured by the autophosphorylation activity of PKR, or by the ability of the kinase to phosphorylate eukaryotic initiation factor-2 (eIF-2).

In another general embodiment, the activity of PKR is determined indirectly, by assaying the test cells for the presence of a functional mutation in PKR, including, but not limited to, inversion, deletion, insertion, and point mutation.

In a third general embodiment, PKR activity is determined indirectly, by measuring the expression of PKR gene, i.e., cellular PKR mRNA concentration and protein concentration.

Also forming part of the invention is a kit for screening human tissue for the presence of neoplastic cells by assaying PKR activity. In one embodiment, the kit includes a solid support having surface bound anti-PKR antibodies, for reaction with a cell extract of test cells to be screened, to bind PKR in the extract to the support, and a reagent mixture which includes adenosine triphosphate (ATP) and double-stranded RNA, for reaction with PKR bound to the support.

In another embodiment, the kit includes a solid support having a surface bound PKR substrate, e.g., eIF-2, bound to a solid surface, and a reagent mixture which includes ATP and double-stranded RNA, for reaction with PKR from the cell extract in the presence of the solid support, to phosphorylate the substrate bound to the solid support.

By PKR expression is meant transcription and translation of PKR gene, the products of which include precursor RNA, mRNA, polypeptide, post-translation processed polypeptide, and any derivative thereof.

By PKR activity is meant generally any biological activity associated with PKR, or any fragment, derivative, or analog of PKR, such as enzymatic activity, specifically including autophosphorylation activity and eukaryotic translation initiation factor 2 (eIF-2) phosphorylation activity.

By normal PKR activity is meant PKR activity as measured from a normalized amount of non-neoplastic, uninfected cells extract. Preferably, by normal PKR activity is meant a range of PKR activity as measured from a normalized amount of non-neoplastic, uninfected cell extracts from like tissues.

By abnormal PKR activity is meant PKR activity statistically different from that of the normal PKR activity, including above normal and below normal PKR activities.

By a functional mutation of PKR is generally meant a mutation that changes PKR activity. Preferably, it means a mutation that changes autophosphorylation activity and eIF-2 phosphorylation activity of PKR. More preferably, it is meant a mutation that reduces autophosphorylation activity and eIF-2 phosphorylation activity of PKR.

In a second aspect, this invention features methods for screening for neoplastic cells by assaying P58 expression, activity, or mutation.

In one general embodiment, P58 activity is determined by measuring the PKR protein kinase inhibitory activity of P58 in cell extract from test cells to be screened. The P58 inhibitory activity may be measured by the ability of P58 to suppress the autophosphorylation activity of PKR, or by the ability of P58 to suppress the phosphorylation of eukaryotic initiation factor-2 (eIF-2) by PKR.

In another general embodiment, the activity of P58 is determined indirectly, by assaying the test cells for the presence of a functional mutation in P58, including, but not limited to, inversion, deletion, insertion, and point mutation.

In a third general embodiment, P58 activity is determined indirectly, by measuring the expression of P58 gene, i.e., cellular P58 mRNA concentration and protein concentration.

In a fourth general embodiment, P58 activity is determined by measuring its binding affinity to PKR. By P58 expression is meant transcription and translation of P58 gene, the products of which include precursor RNA, mRNA, polypeptide, post-translation processed polypeptide, and any derivative thereof.

By P58 activity is meant generally any biological activity associated with P58, or any fragment, derivative, or analog of P58, specifically including P58 inhibitory activity of PKR autophosphorylation and eIF-2 phosphorylation.

By normal P58 activity is meant P58 activity as measured from a normalized amount of non-neoplastic, uninfected cell extract. Preferably, by normal P58 activity is meant a range of P58 activity as measured from a normalized amount of non-neoplastic, uninfected cell extracts from like tissues.

By abnormal P58 activity is meant P58 activity statistically different from that of the normal PKR activity, including above normal and below normal P58 activities.

By a functional mutation of P58 is generally meant a mutation that changes P58 activity. Preferably, it means a mutation that changes P58 inhibitory activity of PKR autophosphorylation and eIF-2 phosphorylation. More preferably, it is meant a mutation that increases P58 inhibitory activity of PKR autophosphorylation and eIF-2 phosphorylation.

By binding affinity is meant the strength of protein-protein interaction between PKR and P58, and fragments and derivatives thereof. Those skilled in the art will recognize methods for measuring said binding affinity.

In a third aspect, this invention features methods for screening for neoplastic cells by assaying anti-P58 activity.

In one general embodiment, anti-P58 activity is measured by the ability of anti-P58 to suppress the P58 inhibitory activity of PKR autophosphorylation and EIF-2 phosphorylation.

In another general embodiment, anti-P58 activity is determined indirectly, by assaying the test cells for the presence of a functional mutation in anti-P58, including, but not limited to, inversion, deletion, insertion, and point mutation.

In a third general embodiment, anti-P58 activity is determined indirectly, by measuring the expression of anti-P58 gene, i.e., cellular anti-P58 MRNA concentration and protein concentration.

In a fourth general embodiment, anti-P58 activity is determined by measuring its binding affinity to P58.

By anti-P58 activity is meant generally any biological activity associated with anti-P58, or any fragment, derivative, or analog of anti-P58, specifically including anti-P58's ability to suppress P58 inhibitory activity of PKR autophosphorylation and/or eIF-2 phosphorylation.

By normal anti-P58 activity is meant anti-P58 activity as measured from a normalized amount of non-neoplastic, uninfected cell extract. Preferably, by normal anti-P58 activity is meant a range of anti-PKR activity as measured from a normalized amount of non-neoplastic, uninfected cell extracts from like tissues.

By abnormal anti-P58 activity is meant anti-P58 activity statistically different from the normal anti-P58 activity, including above normal and below normal anti-P58 activities.

By a functional mutation of anti-P58 is generally meant a mutation that changes anti-P58 activity. Preferably, it means a mutation that changes anti-P58's ability to suppress P58 inhibitory activity of PKR autophosphorylation and EIF-2 phosphorylation. More preferably, it means a mutation that reduces P58 inhibitory activity of PKR autophosphorylation and EIF-2 phosphorylation.

By binding affinity is meant the strength of protein-protein interaction between P58 and anti-P58, and fragments and derivatives thereof. Those skilled in the art will recognize methods for measuring said binding affinity.

In a fourth aspect, this invention features methods for screening compounds for anti-tumor activity.

In one general embodiment, a test compound is added to a system characterized by a below-normal activity of PKR, determining the activity of PKR in the presence of the compound, and selecting the compound if the measured activity of PKR is increased.

In another general embodiment, a test compound is added to a system characterized by an abnormal activity of P58, determining the activity of P58 in the presence of the compound, and selecting the compound if the abnormal activity of P58 is corrected (i.e. made closer to normal).

In a third general embodiment, a test compound is added to a system characterized by an abnormal activity of anti-P58, determining the activity of anti-P58 in the presence of the compound, and selecting the compound if the abnormal activity of anti-P58 is corrected.

In a fourth general embodiment, a test compound is added to a system containing both PKR and P58, determining the binding affinity between PKR and P58, and selecting the compound if the measured binding affinity between PKR and P58 is reduced.

In a fifth general embodiment, a test compound is added to a system containing both P58 and anti-P58, determining the binding affinity between P58 and anti-P58, and selecting the compound if the measured binding affinity between PKR and P58 is increased.

By screening is meant a process in which a large number of potentially useful agents are processed in the methods of this invention. It is generally a process distinct from a single experiment in which a single agent is studied in detail to determine its methods of action.

In a fifth related aspect, the invention features novel anti-tumor agents discovered by the methods described above. It also includes novel pharmaceutical compositions which include anti-tumor agents, discovered as described above, and formulated in pharmaceutically acceptable formulations.

By pharmaceutically acceptable formulation is meant any formulation which can be used in a pharmaceutical composition prepared for storage and subsequent administration, which comprises a pharmaceutically effective amount of an agent as described herein in a pharmaceutically acceptable carrier or diluent. Acceptable carriers or diluents for therapeutic use are well known in the pharmaceutical art, and are described, for example, in *Remington's Pharmaceutical*

Sciences, Mack Publishing Co. (A. R. Gennaro edit. 1985). Preservatives, stabilizers, dyes and even flavoring agents may be provided in the pharmaceutical composition. In addition, antioxidants and suspending agents may be used.

In a sixth aspect, the invention features methods for treating human neoplasms which are characterized by a subnormal activity of PKR, above normal activity of P58, or subnormal activity of anti-P58.

The methods comprise delivering into the neoplastic cells a source of PKR activity or/and a source of anti-P58 activity. In one embodiment, the source may be a wild type PKR gene or/and anti-P58 gene, or native PKR or/and anti-P58.

By delivering is meant the use of any and all methods known to those skilled in the art for administering drugs to the mammal.

Other features and advantages of the invention will be apparent from the following description of the preferred embodiments thereof, and from the claims.

DETAILED DESCRIPTION OF THE PREFERRED EMBODIMENTS

BRIEF DESCRIPTION OF THE DRAWINGS

FIG. 5A–C shows the polynucleotide sequence of wild-type human PKR gene, where the underlined regions indicate forward ($F_1$) and reverse ($R_{1-10}$) primer sequences for amplifying selected regions of the gene sequence, and the boxed regions I–XI and VA indicate catalytic regions of conserved sequences;

FIG. 10, Panel A–B is a DNA sequence and deduced amino acid sequence of the P58 cDNA. Numbers on the left indicate the nucleotides position and numbers on the right indicate amino acid position. The stop codon (TAA is indicated by asterisks. The suboptimal polyadenylation signal (ATTAAA) is underlined.

FIG. 10, Panel C is a DNA sequence of 3' untranslated region of the P58B cDNA. The mRNA instability sequences (ATTTA) are in bold and the polyadenylation signal (AATAAA) is underlined.

Figure 1A:
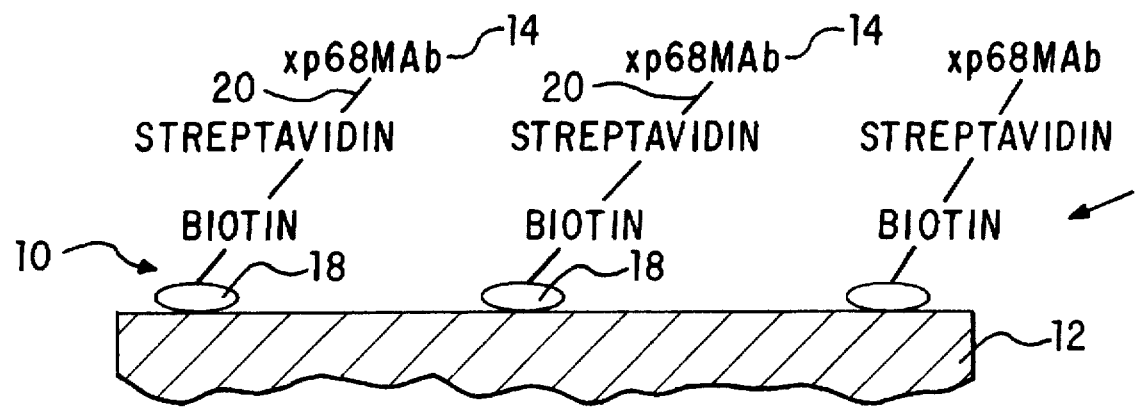
FIGS. 1A–1C illustrate a solid-phase reagent (1A) for use in assaying PKR autophosphorylation, in accordance with the invention, immunospecific binding of PKR to the reagent surface (1B), and phosphorylation of bound PKR on the reagent surface (1C)

The present invention provides novel methods for identifying neoplastic cells, discovering anti-tumor agents, and for preventing or treating neoplasm with the agents discovered. The methods of this invention are based on the observation that PKR, P58, and anti-P58 proteins are implicated in oncogenesis.

PKR is an interferon-inducible cytoplasmic protein with serine-threonine-specific protein kinase activity (Hovanessian, 9 J. Interferon Res. 641, 1989; Meurs et al., 62 Cell 379, 1990). PKR is expressed constitutively at a low level in a large variety of cells. In the literature, PKR has been referred to as dsRNA-activated protein kinase, P1/eIF-2 kinase, DAI or dsI for dsRNA-activated inhibitor, and p68 (human) or p65 (murine) protein kinase.

PKR can be activated by double-stranded RNA (dsRNA), single-stranded RNA with double-stranded segments, or some polyanions such as heparin. Upon activation, PKR autophosphorylates on a serine residue. The autophosphorylated PKR can phosphorylate a serine residue of the alpha subunit of the eukaryotic translation initiation factor eIF-2 (Galabru and Hovanessian, 262 J. Biol. Chem. 15538, 1987), a modification that causes inhibition of protein synthesis (Jagus et al., 25 Prog. Nucleic Acid Res. Mol. Biol. 127, 1981). Through this mechanism, PKR is implicated in the antiviral and antiproliferative effects of interferon.

PKR participates in cell growth and differentiation by regulating protein synthesis. Expression of wild type PKR in yeast has an inhibitory effect on cell growth, as does expression of the tumor suppressor gene p53 (Chong et al., 11 EMBO J. 1553, 1992; Fields and Jand, 249 Science 1046, 1990). Koromilas et al., 257 Science 1685, 1992, hereby incorporated by reference, indicate that transfection into murine NIH 3T3 cells of a mutant human PKR cDNA encoding a protein lacking eIF-2 kinase activity (because of the deletion of a crucial six-amino acid segment) resulted in malignant transformation. When injected into nude mice, these cells produced tumors within 2–4 weeks. In contrast, no tumor growth was observed during this time in mice injected with cells carrying only the endogenous PKR. These results indicate that PKR may function as a suppressor of cell proliferation and tumorgenesis.

PKR is inhibited by P58, a cellular 58-kDa protein purified from influenza virus-infected cells (Lee et al., 267 J. Bio. Chem. 14238, 1992; Lee et al., 87 Proc. Natl. Acad. Sci. USA 6208, 1990; Katze et al., 62 J. Virol. 3710, 1988). P58 inhibits both the autophosphorylation of PKR as well as phosphorylation of the alpha subunit of eIF-2 by the kinase.

P58 itself appears to be inhibited by a cellular anti-P58 protein(s). Lee et al., 267 J. Biol. Chem. 14238, 1992, indicate that some ammonium sulfate fractions of the crude uninfected cell extracts were associated with anti-P58 activity, although the crude uninfected cell extracts showed no detectable anti-P58 activity.

The methods exemplified herein utilize three mechanisms, namely, (i) tumor suppressing activity of PKR, (ii) oncogenicity of P58, and (iii) tumor suppressing activity of anti-P58 protein. The use of these examples is in no way intended to limit the scope of the invention.

Methods which can be used to assay the activity of PKR, P58, and anti-P58 include, but are not limited to, detecting functional mutation (e.g., insertion, deletion, inversion, and point mutation) in a gene, measuring the concentration of mRNA or protein of a gene in cells, measuring enzyme activity of a protein in vitro, measuring interaction between these three proteins, assaying the ability of a gene in transforming a cell line, and assaying the ability of a gene in producing tumor in nude mice. Those skilled in the art will identify other methods for assaying activity of a gene product.

These methods can be applied with a gene cloned in a vector (preferably an expression vector), mRNA of a gene, purified protein, or cell extracts.

I. Methods for Screening for Neoplastic Cells

The present invention provides methods for screening human tissue for the presence of neoplastic cells.

The human tissue screened is typically biopsy tissue obtained from an organ, such as lung, breast, colon, liver, intestine, pancreas, endocrine gland, or neuronal tissue, which is suspected of containing, or which is being tested for the presence of, neoplastic cells. Alternatively, the tissue may include blood cells, such as white blood cells, or subfractions thereof, or bone marrow cells, which are being tested for neoplasm.

By "neoplastic cells" is meant cells which are capable of unregulated growth in vivo, as evidenced by an abnormal rate of cell division and metabolic activity, e.g., rate of DNA synthesis, for that cell type.

Methods of obtaining tissue biopsy material, fractionated blood cells, or bone marrow cells blood are well known. The biopsy or cell material to be tested is lysed, either by homogenization, enzyme treatment, detergent treatment, osmotic lysis or a combination of these methods, to form a cell lysate containing intracellular enzymes in solution form. Typically, the lysate is further treated, e.g., by filtration or centrifugation, to remove intracellular organelles and other particulate matter in the total lysate, yielding a soluble-fraction lysate. One exemplary method for obtaining a soluble-fraction lysate is detailed in Example 1. The lysate is assayed for PKR activity, P58 activity, and anti-P58 activity.

A. Assaying PKR Activity

In one general embodiment, PKR activity is assayed directly, by measuring PKR autophosphorylation activity, or the activity of the kinase in phosphorylating a substrate, preferably eukaryotic initiation factor-2α (eIF-2α), although other factors such as nuclear factor-κB (NF-κB) (Link et al., 267 *J. Biol. Chem.* 239, 1992) may be suitable. The PKR protein is preferably assayed in immunopurified form, using an anti-PKR polyclonal or monoclonal antibody, such as described in Part 1.

Part 2 describes solution-phase methods for assaying PKR activity. Part 3 describes solid-phase assay methods, and two kit embodiments designed for use in the solid-phase methods.

The lysate may be further assayed to provide a quantitative or qualitative measure of PKR or PKR mRNA concentration in the lysate, as discussed in Part 4. In another general embodiment, discussed in Part 5, the activity of PKR in the cell lysate is determined indirectly by detecting mutations in the genomic or transcriptional sequences which encode the PKR protein.

Part 1. Polyclonal and MAb Antibodies against PKR

Polyclonal or monoclonal antibodies specific against PKR may be prepared by conventional techniques. The immunogen used is purified PKR protein or protein fragment, preferably conjugated to a carrier protein. A suitable animal, such as rabbit or mouse, is injected according to immunological protocols generally known in the art, e.g., Harlow, pp. 93–115. Typically, the animal is injected subcutaneously with the immunogen in an adjuvant, and booster immunizations are given by subcutaneous or intramuscular injection every 2–3 weeks. Blood is collected at intervals, e.g. 1–2 weeks after each immunization injection. Antisera may be titrated to determine antibody formation with respect to PKR, according to standard immunoprecipitation methods (Harlow et al., *Antibodies: A Laboratory Manual*, Cold Spring Har Lab, 1988, pp. 423–470).

To prepare a monoclonal antibody MAb specific against PKR, the PKR immunogen described above is used to immunize an animal, such as a mouse, from which antigen-specific lymphocytes can be obtained for immortalization. These methods are used to generate a hybridoma cell line which has a high specificity toward PKR. Briefly, in producing the cell line, mice are immunized by intraperitoneal injection of a PKR immunogen. Several, e.g., 8 weeks after initial immunization, spleen cells are harvested, and fused with a standard myeloma cell line. Selection for successful fusion products is in HAT medium, according to published methods. Successful fusion products are then screened for immunoreactivity with PKR, by antigen capture in solution by immunoprecipitation. Cell lines which show high affinity binding to PKR may be subcloned by limiting dilution and further screened for production of antibodies with high binding affinity for PKR. Antibody producers whose antibody binding to PKR does not inhibit autophosphorylation activity of the enzyme are selected.

To produce the antibody reagent, the hybridoma cell line is grown in a suitable medium, such as Dulbecco's modified Eagle's (DME) or RPMI 1640 media. MAbs are harvested from the medium and can be concentrated and stored according to published methods (Harlow pp. 271–318, supra). A monoclonal antibody (MAb) specific against PKR and whose binding to PKR does not interfere with PKR autophosphorylation activity, or eIF-2 phosphorylation activity has been reported (Laurent, et al., 125 *Biochem. Biophys. Res. Comm.* 1, 1984; Laurent, et al., 82 *Proc. Natl. Acad. Sci. USA* 4341, 1985).

Part 2. Assaying PKR Kinase Activity: Solution Phase Format

Since the cell lysate, including the soluble-fraction lysate used in the assay, may contain a number of different protein kinase enzymes, it is desirable to assay the PKR activity in purified or partially purified form. A variety of methods, including chromatographic separation methods, are available for this purpose. In a preferred method, the PKR is immunopurified by immunoprecipitation with affinity binding to an anti-PKR antibody (Part 1).

In one embodiment of the method, for use in measuring PKR autophosphorylation activity in a solution-phase format, the lysate is treated with free antibody to form an immunoprecipitate, and the precipitate is isolated and washed by standard methods, such as detailed in Example 1. The washed material is then added to a reaction mixture containing radiolabeled ATP and a PKR activator, such as dsRNA or heparin, with the reaction being carried out typically over a 30–60 minute time period at room temperature. Following the reaction, the immunoprecipitated PKR material may be captured, e.g., by filtration, and assayed for phosphorylation level by scintillation counting.

Alternatively, the immunoprecipitate may be solubilized, e.g., in sodium dodecyl sulfate (SDS) and separated on SDS-polyacrylamide gel electrophoresis (SDS-PAGE). The band corresponding to PKR can be assayed in the gel by autoradiography (illustrated in Example 4), or can be eluted from the gel for assay by scintillation counting, according to standard methods.

A related solution-phase format can be employed for assaying the activity of PKR in phosphorylating a natural cellular translation factor, such as eIF-2, or other known protein kinase substrates, such as NF-κB (Link et al., supra). In this method, described in Example 2, lysate PKR, preferably in immunopurified form, is added to a reaction mixture containing radiolabeled ATP, dsRNA or heparin, to activate the enzyme, and the protein substrate. The phosphorylation reaction is carried out as above, as is detection of radiolabeled substrate (illustrated in Example 4).

For both the autophosphorylation or substrate-phosphorylation reaction methods, one important control is the measured activity of PKR obtained from normal cells, preferably cells of the same type as those being screened. This control may be standardized for various cell types, thereby avoiding the need to run this control with each sample. In accordance with the invention, a measured PKR activity which is substantially less than normal-cell PKR activity is diagnostic of neoplastic cells, or cells which are predisposed to a neoplastic condition.

A second appropriate control is the assay reaction performed in the absence of PKR activator, e.g., double-stranded RNA (dsRNA) or heparin. This control provides a good measure of background radiolabeling which is produced in the absence of enzyme activation.

Part 3. Assaying PKR Kinase Activity: Solid-Phase Format

Figure 1B:
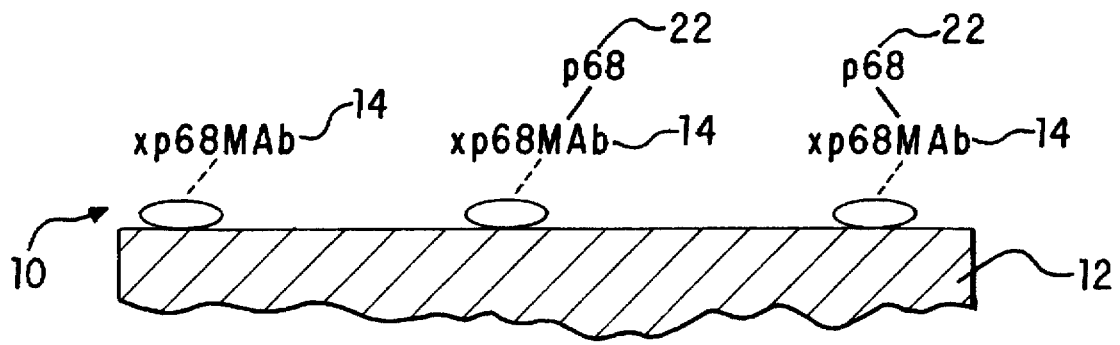
Figure 1C:
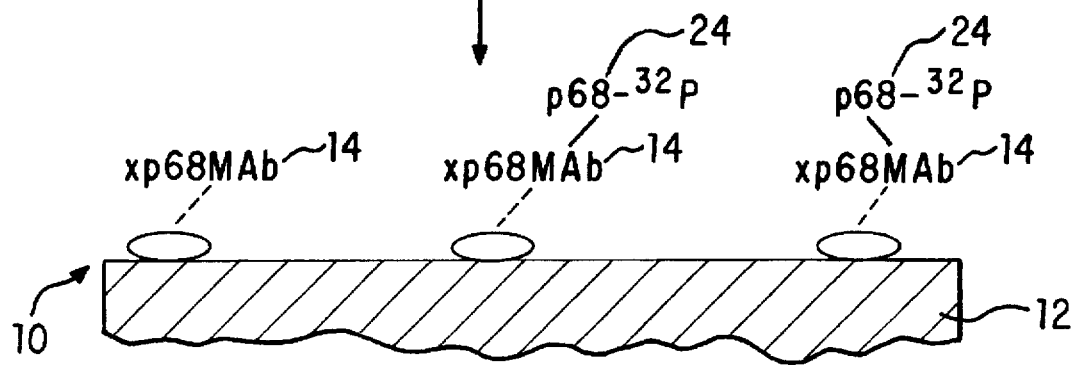

FIGS. 1A–1C illustrate reagent components for carrying out the assay method of the invention, in this case for determination of PKR autophosphorylation activity, in a solid-phase format. FIG. 1A shows a solid-phase reagent 10 composed of a solid support 12 coated with surface bound anti-PKR antibody molecules, indicated at 14. The antibodies are attached to the support by first adsorbing an ovalbumin-biotin complex, indicated at 18 in FIG. 1A, to the support surfaces, then attaching an anti-PKR-antibody-streptavidin complex, indicated at 20 in FIG. 1A, to the adsorbed biotin. The protein conjugation methods employed in the construction of the solid-phase reagent follow well-known methods (Wong, S. S., *Chemistry of Protein Conjugation and Crosslinking*, CRC Press, 1991).

In carrying out the reaction method, the solid-phase reagent is contacted with cell lysate under conditions which allow immunoreaction of PKR in the lysate with the support-bound antibodies. Following the reaction, the support is washed to remove non-specifically bound material. The solid-support reagent now contains immunospecifically bound PKR molecules, indicated at 22 in FIG. 1B.

The reagent is now reacted with radiolabeled ATP and activator, e.g., heparin, under conditions which allow autophosphorylation of the antibody-bound PKR enzyme, leading to radiolabeling of the support-bound enzyme molecules, indicated at 24 in FIG. 1C. Enzyme activity is then assayed by scintillation counting of the labeled region of the solid support.

The reagent components described above are part of an assay kit according to another embodiment of the invention. The kit generally includes a solid support 10 having surface bound anti-PKR antibodies, for reaction with a cell lysate of test cells to be screened, to bind PKR in the lysate to the support, and a reagent mixture which includes ATP and activator, such as double-stranded RNA or heparin, for reaction with PKR bound to the support.

Figure 2A:
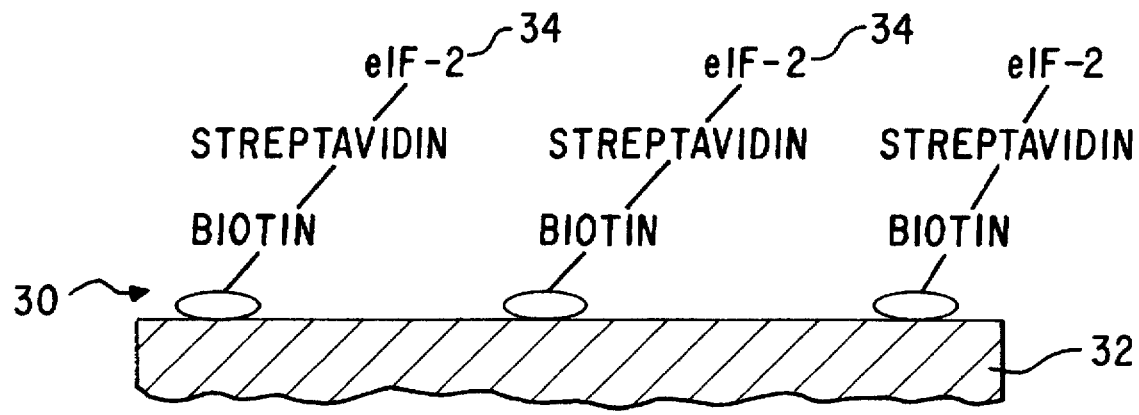
FIGS. 2A–2C illustrate a solid-phase reagent (2A) for use in assaying PKR eIF-2 phosphorylation, in accordance with the invention, immunopurification of PKR from cell lysate (2B), and phosphorylation of eIF-2 attached to the solid-phase reagent (2C)
Figure 2B:
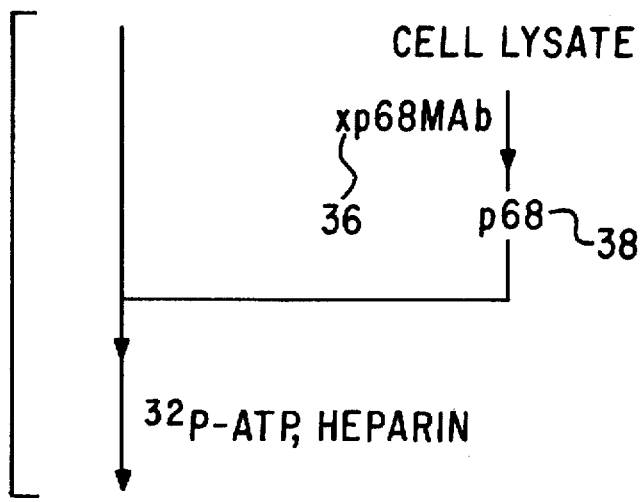
Figure 2C:
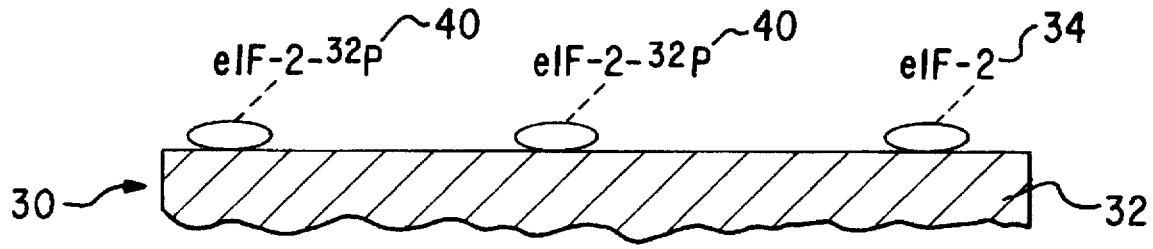

FIGS. 2A–2C illustrate reagent components for carrying out the assay method of the invention, for determination of PKR substrate phosphorylation activity, in a solid-phase format. FIG. 2A shows a solid-phase reagent 30 composed of a solid support 32 coated with surface bound eIF-2 substrate molecules, indicated at 34. The eIF-2 molecules are attached to the support through a biotin-avidin configuration, such as described above with respect to FIGS. 1A–1C.

In carrying out the reaction method, the cell lysate is first reacted with a free anti-PKR antibody, indicated at 36 in FIG. 2B, and the immunoprecipitate is isolated to yield a purified PKR, indicated at 38 in FIG. 2B.

The solid-support reagent is now reacted with the PKR immunoprecipitate, radiolabeled ATP, and heparin, under conditions which allow phosphorylation of the support-bound eIF-2 substrate. The reaction product is radiolabeled support-bound EIF-2 molecules, indicated at 40 in FIG. 2C. Enzyme activity is then assayed by scintillation counting of the labeled region of the solid support.

The reagent components described above form an assay kit according to an alternate kit embodiment of the invention. The kit generally includes a solid support 30 having surface bound EIF-2 molecules, for reaction with immunopurified PKR. Also included in the kit is (i) an anti-PKR antibody for immunopurifying PKR from a cell lysate, and a reagent mixture which includes ATP and activator, for reaction with PKR in the presence of substrate.

In both of the above solid-phase formats, the two controls described above with respect to the solution-phase assay methods are carried out in parallel with the test-cell assays.

Part 4. Assaying PKR Level

As noted above, the method of determining PKR activity in the cells screened may also include measuring the quantity of PKR protein or mRNA in the cells being screened. The measured level may be useful in determining whether a low measured activity of PKR is due to a defective PKR enzyme or to low levels of expression of the enzyme.

Figure 3:
FIG. 3 is an autoradiograph of an immunoblot of PKRPK from NIH 3T3 cells.

Example 3 describes an immunoblot method for assaying PKR levels in a cell lysate. In this method, cell lysate is fractionated by SDS-PAGE, the separated proteins are transferred to a nitrocellulose membrane, and the membrane is reacted with an anti-PKR antibody. The antibody, or a secondary antibody which is immunoreactive with the anti-PKR antibody, is labeled, e.g., with a conjugated enzyme, for detecting the PKR band on the membrane. FIG. 3 shows an immunoblot of PKR obtained from a cell lysate. Although the method gives a single immunoreactive band, the density of the band provides only a rough approximation of actual PKR levels.

A more quantitative method for determining PKR levels can be achieved by iodinating immunoprecipitated PKR. In this method, cell lysate is reacted with an anti-PKR antibody captured on a solid support, such as the support described above with reference to FIGS. 1A–1C. After extensive washing to remove non-specifically bound material, the proteins on the support (antibody and captured PKR) are iodinated, using standard methods (e.g., Harlow, p. 324, supra). The iodinated PKR is released from the support, e.g., by detergent treatment, and the released iodinated protein is quantitated by scintillation counting.

In still another approach, lysate PKR levels can be quantitated in a competitive antibody binding assay in which lysate PKR and reporter-labeled PKR compete, in a lysate mixture, for binding to a limiting number of antibody sites on a solid support coated with anti-PKR antibody, such as described above with respect to FIGS. 1A–1C. The lysate PKR level is determined from the extent of reporter binding to the solid support.

Part 5. Detecting PKR Mutations

In a second general aspect, the activity of PKR, as a marker for neoplastic cells, is assayed by examining the cells for mutation in one or both alleles of the PKR genes. This section discloses a number of assay formats which can be employed for this purposes.

(a) In vitro Translated PKR mRNA

In one method, mRNA isolated from the test cells is examined for the ability to express active PKR in a cell-free synthesizing system. Detailed method for this approach is given in Example 4. Briefly, total mRNA isolated from test-cell lysate is added to a cell-free protein synthesizing system, and the system is reacted under conditions which allow active translation of added mRNA. The translation products are immunoprecipitated, and are assayed for protein kinase activity, as above.

Figure 4:
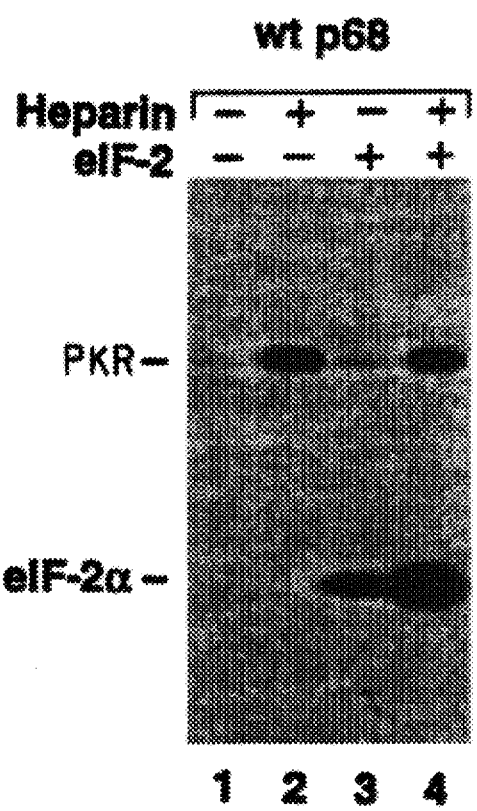
FIG. 4 is an autoradiograph showing functional activity of PKR in vitro, measured for capped PKR transcripts translated in a cell free protein synthesis system, immunoprecipitated, then reacted with [-$^{32}$P]ATP in the presence (+) or absence (–) of heparin and eIF-2, as indicated, after fractionating by SDS-PAGE.

In the method described in Example 4, PKR-PT immunoprecipitate was assayed in the presence of $^{32}$P-ATP, and in the presence (+) or absence (−) of heparin (as activator) and eIF-2, in indicated in FIG. 4. The reaction material was fractionated by SDS-PAGE and the two phosphorylated protein bands (PKR and eIF-2) were visualized by autoradiography. Similar work-up of mRNA known to contain a deletion mutation gave no visible bands. Thus, the method is effective to detect cells which are deficient in an mRNA species (or gene) which expresses an active PKR.

(b) PKR Gene Insertion or Deletion Mutations

Figure 5A:
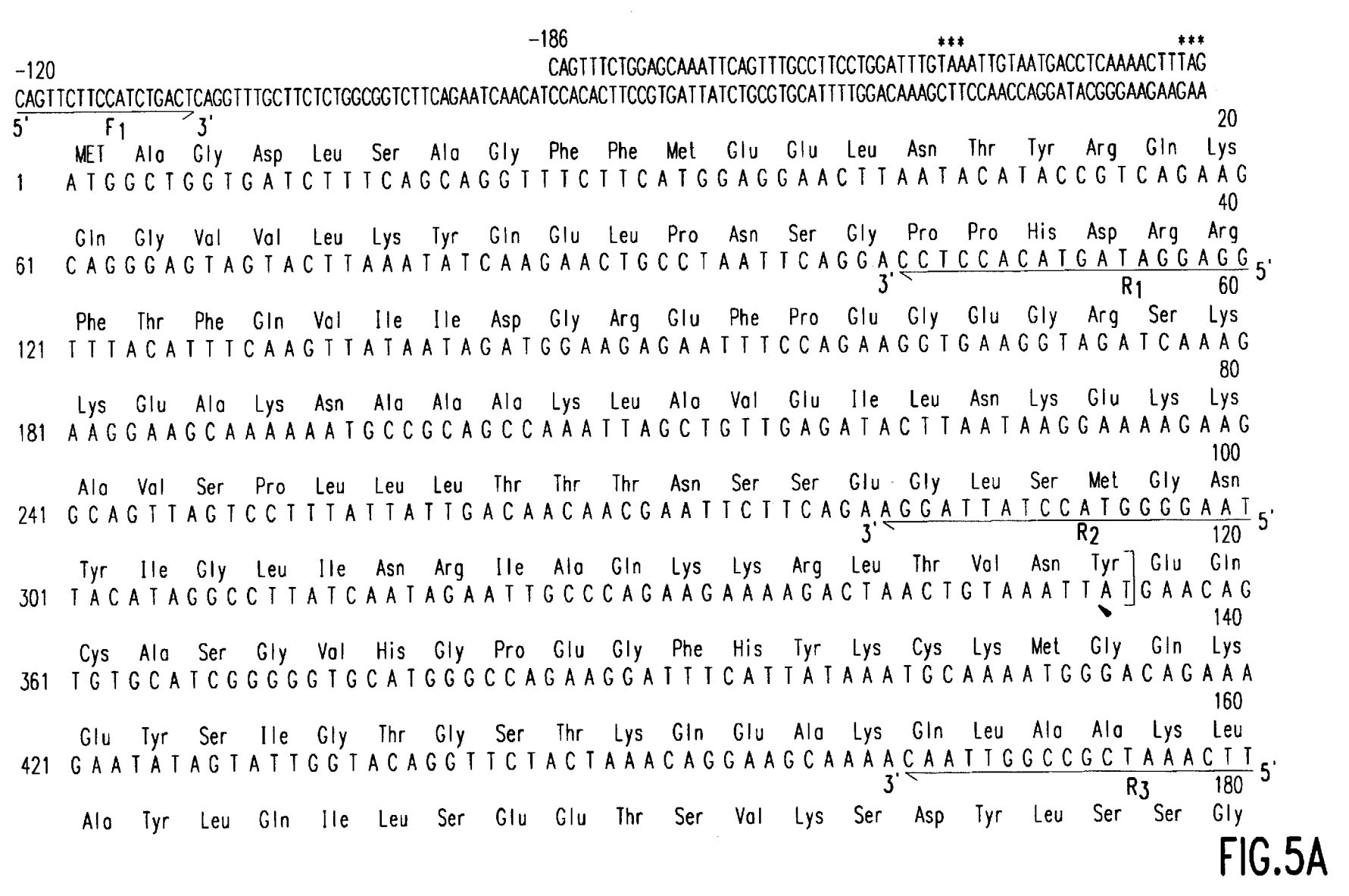
Figure 5B:
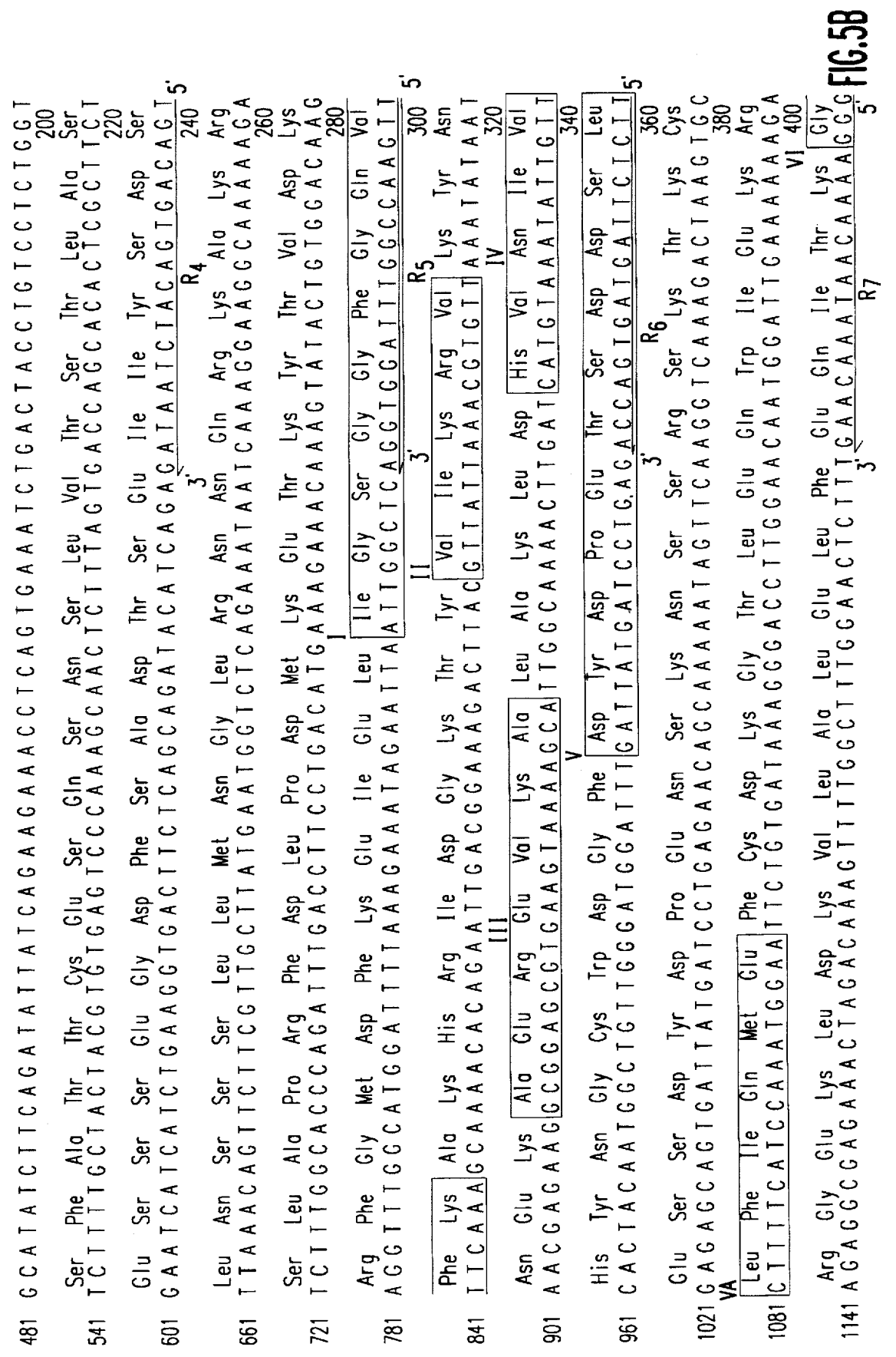
Figure 5C:
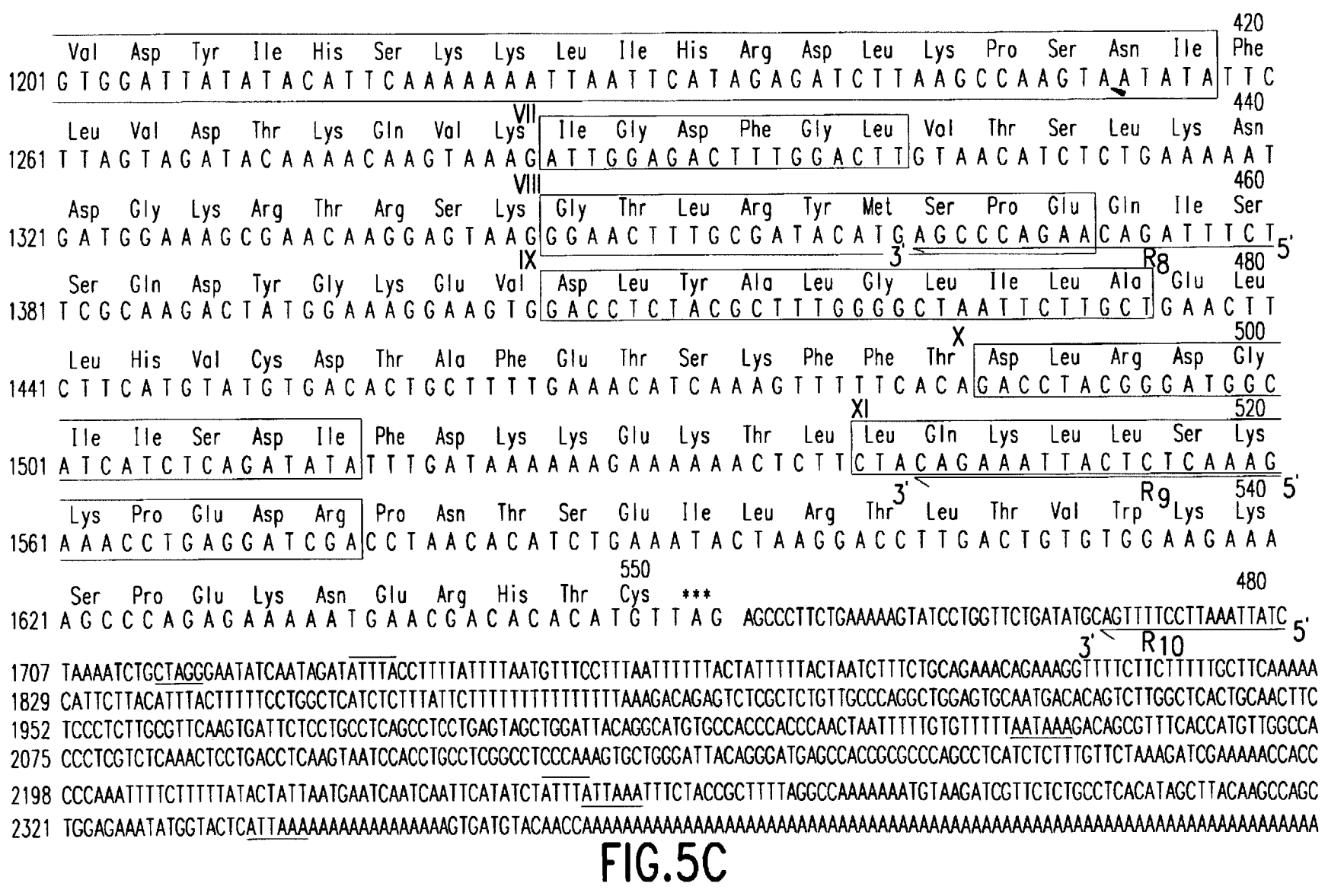

In this embodiment, polymerase chain reaction (PCR) methodology is used to detect insertion or deletion mutations in one or more selected coding regions of the human PKR gene. The coding sequence of the gene is shown in FIG. 5A–C and is identified herein as SEQ ID NO. 1, extending from base 1 to 1653. In the method illustrated herein, the coding sequence, plus sequences upstream and downstream of the coding region, are divided into 10 regions. The first region is bounded upstream by the sequence shown in underlining, this primer being defined as forward primer $F_1$. The region is bounded downstream by the sequence which is underlined and indicated as reverse primer $R_2$. The first region includes about 240 bases. The second region includes an additional 180 bases, extending from $F_1$ to reverse primer $R_1$, and includes the first region plus an additional 180 bases. Each additional region includes an additional 180 bases, being defined at its downstream end by one of the reverse primers $R_i$ shown in underlining. It will be appreciated that forward primer $F_1$ has the sequence shown in underlining in the figure, and reverse primers $R_1R_{10}$ have sequences which are complementary to the sequences shown. These primer sequences are identified herein as follows:

$F_1$: SEQ ID NO 2; $R_1$: SEQ ID NO 3; $R_2$:SEQ ID NO 4; $R_3$: SEQ ID NO 5; $R_4$: SEQ ID NO 6; $R_5$: SEQ ID NO 7; $R_6$: SEQ ID NO 8; $R_7$: SEQ ID NO 9; $R_8$: SEQ ID NO 10; $R_9$: SEQ ID NO 11; $R_{10}$: SEQ ID NO 12.

The 11 primers are constructed by conventional solid-phase synthesis methods, and each primer preferably includes a terminal restriction site, such as an AluI sequence, at which amplified gene regions can be "trimmed" by restriction digestion.

In practicing the method, genomic DNA or mRNA transcripts are isolated from test cell lysates according to standard methods. Genomic DNA may be fragmented or restriction digested by standard procedures. In the case of mRNA isolation, first strand cDNA synthesis is carried out using a commercially available cDNA kit (Boehringer-Mannheim, Indianapolis, Ind.) or standard methods employing reverse transcriptase and random hexamers.

Genomic DNA or cDNA prepared by the above-described procedures is then mixed with the 11 primers (forming 10 primer pairs) indicated above, and the mixture is carried through several (e.g., 20) thermal cycles in the presence of a heat stable polymerase in a PCR reaction mixture, as described in commercially available instructions (Perkin-Elmer Cetus PCR kit; Norwalk, Conn.). Reaction products are preferably subjected to gel purification, then fractionated by gel electrophoresis under denaturing conditions. Separated gel products are transferred to blotting material such as a nylon sheet, and the bands are visualized by hybridization with a radiolabeled PKR oligonucleotide probe (which hybridizes to the upstream most region), and autoradiography.

Figure 6:
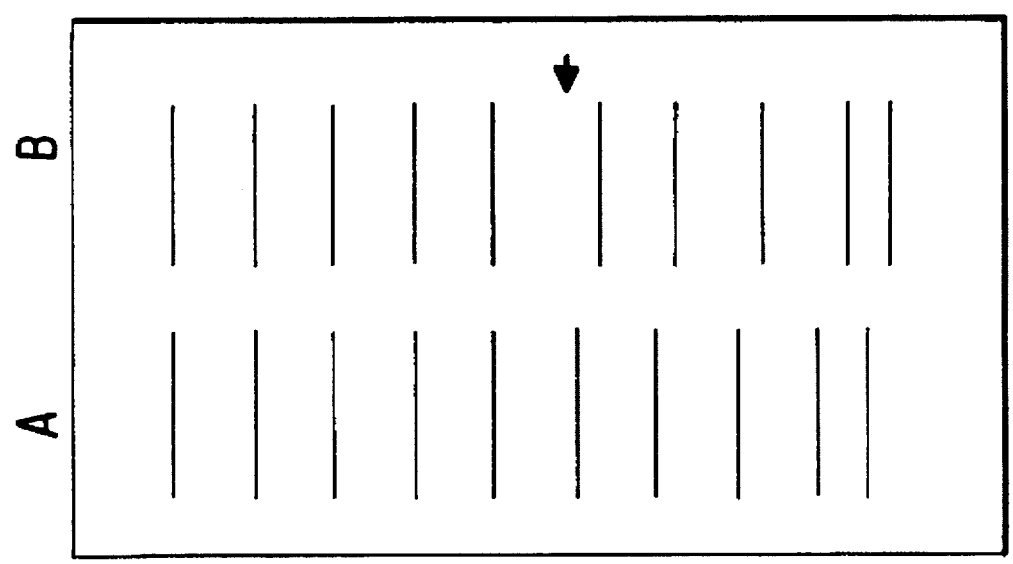
FIG. 6 is an idealized gel pattern of PCR-amplified regions 1–10 of a PKR-KT wildtype gene (lane A) and the same regions in a mutant PKR gene having a deletion in a gene having a deletion mutation in region 5 of the gene (lane B)
Figure 8:
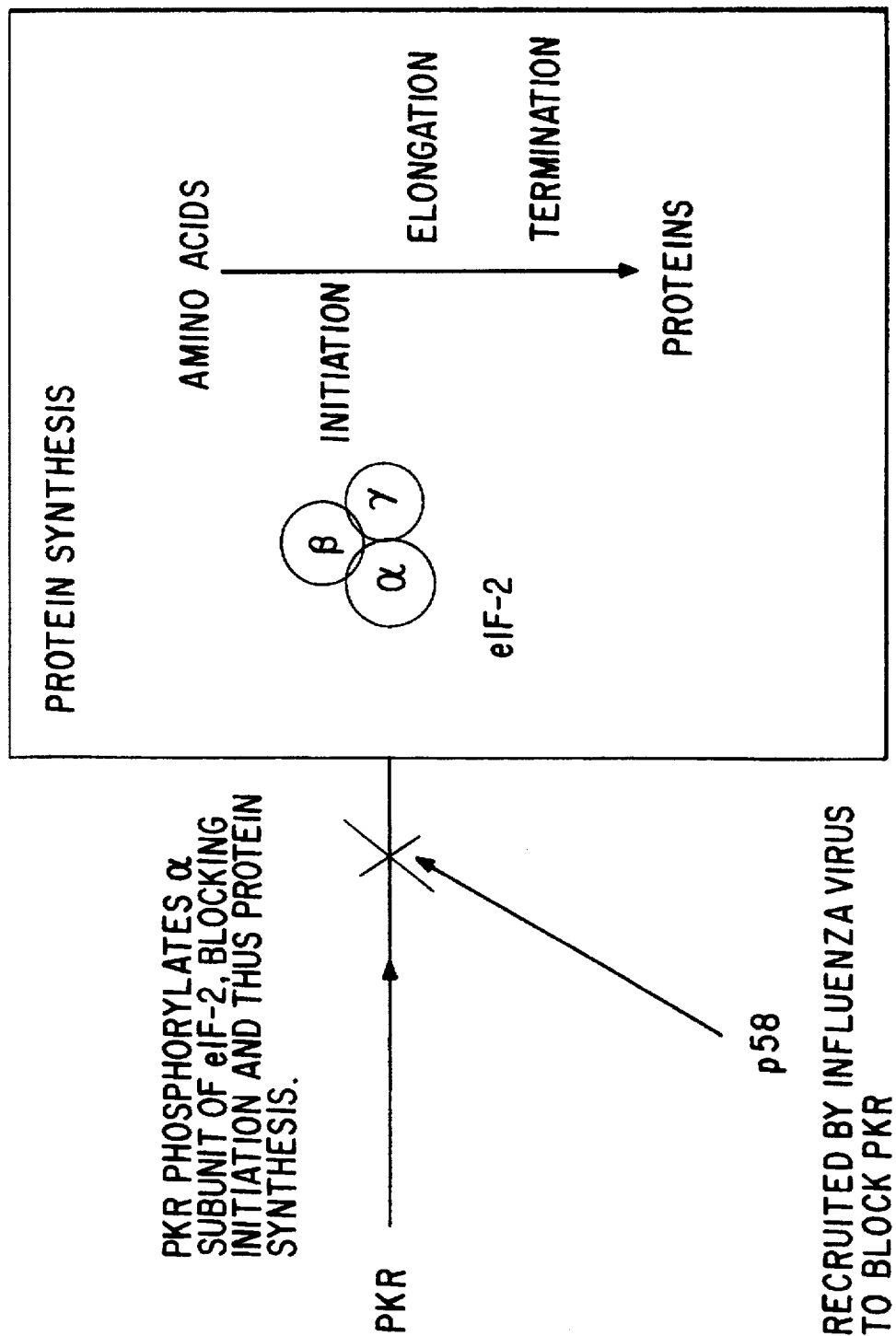
FIG. 8 is a schematic representation of roles played by PKR and P58 in viral infection. PKR is activated by double stranded RNA (typically introduced into, or produced in, a cell during vital infection); its activation shuts down protein synthesis, preventing viral replication. Various viruses have evolved different mechanisms to inhibit PKR and/or its activation. In the case of influenza virus, this is achieved by recruitment of P58, a cellular protein which inhibits PKR and its activation.

FIG. 6 shows idealized gel patterns of amplified PKR gene regions 1–10 from wildtype (lane A) PKR gene and a mutant gene containing a deletion mutation in gene region 6. The 10 bands from the wildtype gene migrate at the expected, logarithmically spaced size ranges of the 10 amplified fragments. The positions of the bands in the test sample (lane B) correspond to the wildtype position in each region 1–5, but migrate ahead of the corresponding wildtype bands in regions 6–10, due to the smaller fragment size. The position and extent of a deletion or insertion mutation, e.g., in the 6th region, can be determined, if desired, by standard sequencing methods, e.g., dideoxy sequencing (Sanger et al., 74 Proc. Natl. Acad. Sci. USA 5463, 1977).

The method of restriction fragment-length polymorphisms (RFLPs) may also be employed for detecting insertion or deletion mutations, using PCR amplified PKR gene fragments. Suitable restriction sites can be selected from the known wildtype coding sequence, according to well-known strategies.

(c) PKR Gene Point Mutations

This section considers two general methods for detecting small mutations in a human PKR gene, including substitutions, deletions or insertions of one (point mutations) or a small number of bases in the gene. Both methods involve basepair mismatches with a reporter-labeled probe or probe pair.

In one method, mismatch between a single-stranded genomic fragment region or a mRNA and a labeled RNA probe allows for selective probe cleavage at the site of the mismatch, according to known methods (Winter et al., 82 Proc. Natl. Acad. Sci. USA, 7575, 1985; Meyers et al., 230 Science 1242, 1985). As an example, the PKR gene is known to contain conserved catalytic regions I–XI (Meurs et al., 62 Cell 379, 1990; Feng et al., 89 Proc. Natl. Acad. Sci. USA 5447, 1992; Ramirez et al., 11 Mol. Cell. Biol. 3027, 1991; Chong et al., 11 EMBO J. 1553, 1992; Chen et al., 89 Proc. Natl. Acad. Sci. USA 7729, 1991; and Hanks et al., 200 Methods Enzymol. 38, 1991), as shown in boxes in FIG. 5 (a 12 region VA is also shown in the figure).

The method employs RNA probes which are complementary to the 12 polynucleotide sequence shown in boxes in FIG. 5A–C. These RNA sequences, indicated $Pr_I$–$Pr_{XII}$ are identified herein as follows:

$PrI_I$: SEQ ID NO 13; $Pr_{II}$: SEQ ID NO 14; $Pr_{III}$: SEQ ID NO 15; $Pr_{IV}$: SEQ ID NO 16; $Pr_V$: SEQ ID NO 17; $Pr_{VI}$: SEQ ID NO 18; $Pr_{VII}$: SEQ ID NO 19; $Pr_{VIII}$: SEQ ID NO 20; $Pr_{IX}$: SEQ ID NO 21; $Pr_X$: SEQ ID NO 22; $Pr_{XI}$: SEQ ID NO 23; $Pr_{XII}$: SEQ ID NO 24

The 12 RNA probes are hybridized with single-stranded genomic DNA fragments, mRNA, or with cDNA from test cells, as above. After hybridization, the nucleic acid fragments are treated with RNase A, which acts to digest RNA only where mismatches with the complementary DNA strands occur.

Figure 7:
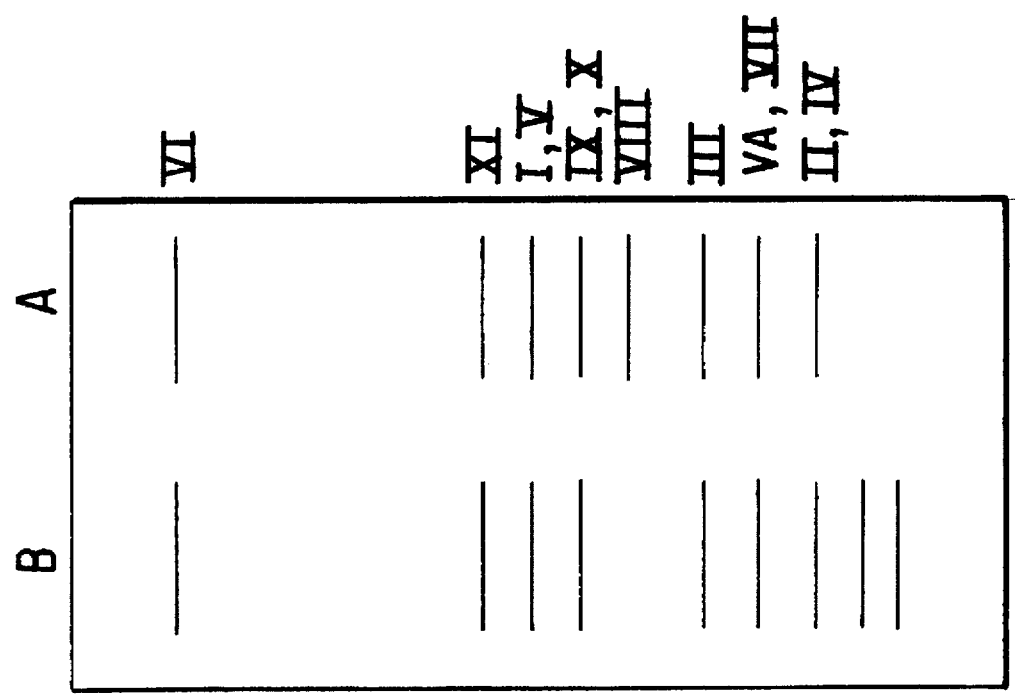
FIG. 7 is an idealized gel pattern of radiolabeled RNA probes used in identifying point mutations in a wildtype PKR gene (lane A) and in a gene having a point mutation in region III (lane B).

After RNA digestion, the RNA probes are fractionated by gel electrophoresis under denaturation conditions, and the gel is developed by autoradiography. FIG. 7 illustrates idealized gel patterns of the 12 probes used in the method. Lane A shows the expected pattern of probes from wildtype gene, where each probe $Pr_i$ migrates according to its original basepair length. Lane B shows the expected pattern of probes where a mismatch has occurred in region XIII, giving rise to 2 smaller bands, as seen. As above, the position and extent of the mutation can be determined by probe sequencing.

In an alternative method, known as oligonucleotide ligation assay (OLA), two probes or probe elements which span a target region of interest are hybridized with a target region of interest, in this case one of the coding regions of the PKR gene. Where the probe elements match (basepair with) adjacent target bases at the confronting ends of the probe elements, the two elements can be joined by ligation, e.g., by treatment with ligase (Winn-Deen et al., 37 Clin. Chem., 1522, 1991). The ligated probe element is then assayed, evidencing the presence of the target sequence. If a probe mismatch occurs at the ligation site, no ligated probe is produced, evidencing a point mutation at the site corresponding to the probe-ligation site.

Alternatively, the ligation method may be carried out under hybridization stringency conditions which prevent probe binding to the target region when base mismatching occurs. Here again, a ligated probe is observed only when complete base pairing of the two adjacent probes with the spanned target region occurs, and failure to observe a ligated probe is evidence of a point mutation.

In one exemplary method, reporter-labeled DNA probe pairs which span each of the above coding regions I–XII in the PKR gene are employed. The pairs are mixed with genomic fragments, prepared as above, preferably under stringent hybridization conditions. After hybridization, the probes are ligated, and fractionated by gel electrophoresis under denaturation condition. The positions of the labeled probes indicates the presence or absence of a mutation within each of the gene regions examined.

EXAMPLE 1

Assaying PKR Autophosphorylation Activity

Cells lysates from a tissue being screened are prepared according to standard methods. Briefly, cells (corresponding to about $1 \times 10^7$ cells) are washed in ice-cold buffer (10 ml) containing 10 mM tris-HCl (pH 7.7), 6 mM $MgCl_2$, 80 mM KCl, 2 mM DTT, 250 mM sucrose, and 0.1 mM EDTA, packed by centrifugation at 600 g for 5 minutes, and lysed by the addition of an equal volume of the above-buffer containing 0.2% Triton X-100 (Petryshyn et al., 259 J. Biol. Chem. 14736, 1984; Petryshyn et al., 85 Proc. Natl. Acad. Sci. USA 1427, 1988). The lysate is centrifuged at 10,000 g for 10 minutes and the soluble fraction (S10 lysate) is stored at $-85°$ C.

The S10 lysate (1 ml) is incubated for 1 hr with a mouse MAb to PKR (Laurent et al., 82 Proc. Natl. Acad. Sci. USA 4341, 1985). The amount of MAb added corresponds to 10–100 l tissue culture supernatant per ml lysate, and can be optimized by titrating the antibody, and determining the amount of material precipitated. The reaction mixture is allowed to stand at room temperature for 1 hour, then cooled on ice for ½ hour.

a) Autophosphorylation Assay in Solution Phase

Immunoprecipitate is collected by standard methods, e.g., by addition of S. aureus Cowan and centrifugation (Harlow, p. 467, supra). The immunoprecipitate is assayed for kinase activity by incubating the precipitate with [$-^{32}$P]ATP (final concentration of 1.25M) in the presence (+) or absence (−) of heparin (10 U/ml) as activator, in a final volume of 0.1 ml reaction buffer, according to published methods (Katze et al., 11 Mol. Cell. Biol. 5497, 1991). The reaction is carried out for 15 minutes at 30° C., and stopped by placing the reaction mixture on ice.

The immunoprecipitate is solubilized in 1% SDS and fractionated on 10% SDS-PAGE, and the gel bands developed by autoradiography on x-ray film for 12 to 15 hours. The extent of phosphorylation of PKR band is determined by scanning the PKR peak in the autoradiograph.

b) Autophosphorylation Assay in Solid Phase

Immunoprecipitate from above is collected on protein-A glass beads, by incubating the beads with the immunoprecipitate for 1 hr at 4° C. (Harlow, p. 468, supra). After washing the beads (3× with PBS), the bound immunoprecipitate is assayed for kinase activity by incubating the precipitate with [$-^{32}$P]ATP (final concentration of 1.25M) in the presence (+) or absence (−) of heparin (10 U/ml) as activator, in a final volume of 0.1 ml reaction buffer, as above. As above, the reaction is carried out for 30 ° C. for 15 minutes.

Following the kinase reaction, the beads are again washed several times to remove non-specifically bound material, and the extent of autophosphorylation is determined by scintillation counting of the washed beads. Background control is provided by a sample which contains all of the reaction components except heparin.

EXAMPLE 2

Assaying PKR eIF-2 Kinase Activity

Cell lysates from a tissue being screened are prepared, and PKR from the lysate, immunoprecipitated with mouse anti-68-PK MAb, as detailed above.

The PKR immunoprecipitate from above is assayed for eIF-2 kinase activity by incubating the immunoprecipitate with [$\gamma$-$^{32}$P]ATP (final concentration of 1.25 microM) in the presence (+) or absence (−) of heparin (10 U/ml) as activator, and purified eIF-2 (0.5 g) a final volume of 0.1 ml reaction buffer, according to published methods (Katze et al., 11 Mol. Cell. Biol. 5497, 1991). The reaction is carried out for 15 minutes at 30 ° C., and stopped by placing the reaction mixture on ice.

The immunoprecipitate is removed from the reaction mixture, e.g., by centrifugation, the soluble material is fractionated by electrophoresis, and used to expose against x-ray film for 12–15 hours. Phosphorylation of the eIF-2 band is determined by scanning the eIF-2 peak (about 38 kilodaltons) in the autoradiograph.

EXAMPLE 3

Immunoblot Determination of PKR Levels

NIH 3T3 cells ($1 \times 10^7$) were washed three times with cold PBS (140 mM NaCl, 15 mM $KH_2PO_4$ pH 7.2, and 2.7 mM KCl) and incubated on ice with an equal volume of 2× lysis buffer (2% Triton X-100, 100 mM KCl, 20 mM tris-HCl pH 7.5), 2 mM dithiothreitol (DTT), 4 mM $MgCl_2$, 0.4 mM phenylmethylsulfonyl fluoride (PMSF) and aprotinin (0.1 mg/ml). The lysate was centrifuged at 10,000 g for 10 minutes, and portions containing equal amounts of protein were subjected to electrophoresis on an SDS-9% polyacrylamide gel.

The separated proteins were transferred to a nitrocellulose membrane (Scheicher & Schuell) in 25 mM tris-HCl (pH 7.5), 190 mM glycine, and 40% (v/v) methanol for 2 hours at 1 Å. The filters were first incubated with 5% (w/v) non-fat dried skimmed milk powder in PBS for 1 hour at room temperature and then with PBS containing a mouse MAb to PKR (Laurent, et al., 1985, supra) 0.5% (v/v) Triton X-100, and 25% PBS for 1 hour. The blot was incubated in 10 ml of PBS containing 10 Ci of $^{125}$I-labeled goat antibodies to mouse immunoglobulin G (New England Nuclear) and 0.5% Triton X-100 for 1 hour, followed by x-ray film for 12 to 15 hours. The immunoblot shows a single peak of molecular weight about 68 Kdaltons (FIG. 3).

EXAMPLE 4

Expression of PKR mRNA

PKR-pcDNAI/NEO plasmid (Katze et al., 11 Mol. Cell. Biol. 5497, 1991) was linearized with Eco RV, and capped transcripts were generated by T7 polymerase in the presence of m$^7$GpppG (Melton et al. 12 *Nucleic Acids Res.* 7057, 1984). After immunoprecipitation with a MAb to PKR (Galabru et al., 262 *J. Biol. Chem.* 15538, 1987; Galabru et al., 178 *Eur. J. Biochem.* 581, 1989), proteins were tested for kinase activity (Katze et al., 11 Mol. Cell. Biol. 5497, 1991) by incubation with [γ-$^{32}$P]ATP in the presence (+) or absence (−) of purified eIF-2 (0.5 µg), with heparin (10 U/ml) as activator, as indicated in FIG. 4. Immunoprecipitates were subjected to electrophoresis on an SDS-10% polyacrylamide gel and autoradiography. The positions of molecular mass standards (in kilodaltons) are shown on the right in FIG. 4.

EXAMPLE 5

Oncogenesis by PKR Point Mutation

Meurs et al., 90 Proc. Natl. Acad. Sci. USA 232, 1993, hereby incorporated by reference, have investigated the potential for tumorgenicity in mice of murine NIH 3T3 clones expressing human PKR kinase. Both the wild-type and a mutant inactive kinase with a single amino acid substitution in the invariant lysine-296 in the catalytic domain II were introduced into nude mice. Expression of the mutant PKR gave rise to the production of large tumors of at least 1 cm in diameter within 7–12 days in all inoculated mice. In contrast, no tumor growth was observed for several weeks in mice inoculated with NIH 3T3 cell clones expressing either the wild-type recombinant PKR kinase, or only the endogeneous p65 kinase (the murine analogue of the PKR kinase). These results suggest that a functional PKR may be a tumor suppressor.

Only much later, very few of the mice injected with the cells carrying the transfected wild-type PKR cDNA did form tumors. The tumor cells recovered were, however, shown to contain PKR devoid of activity. This suggests that naturally occurring mutations in the transfected PKR cDNA might have been responsible for the tumorigenesis (Meurs et al., 1993, supra).

B. Assaying P58 Activity

P58 activity within test cells may be measured by the ability of cell extracts, a fraction of the cell extracts, or purified P58 protein from the cell extracts in inhibiting PKR protein kinase activity, i.e., PKR autophosphorylation and/or phosphorylation of eIF-2 by PKR. In a preferred embodiment, P58 activity is assayed in a purified or partially purified form.

As a general example, an extract of test cells or a fraction of the extract is mixed with a system containing PKR activity, such as purified PKR or PKR-containing cell extract. One can then measure PKR activity according to the methods described in this Application. Purified or partially purified P58 can be prepared from human tissue cells using the method described in Example 6, substituting bovine cells with the human tissue cells. The expression level of P58, i.e. mRNA and protein concentrations can be assayed by the method described in Part 4 above. P58 mutations can be assayed by the method described in Part 5 above.

P58 does not function as a protease, phosphatase, or ATPase. Further, P58 does not degrade or sequester dsRNAs nor does it compete for dsRNA binding sites. It is likely that P58 inhibits PKR through a direct interaction since P58 blocks both the autophosphorylation of PKR in addition to the phosphorylation of the eIF-2 alpha subunit. Thus one assay measures the binding affinity between a wild-type PKR and P58 purified from test cells, using methods recognized by those skilled in the art.

EXAMPLE 6

Cloning, Sequencing, and Expression of P58

(a) Preparation of P58 from Bovine Cells

Madin-Darby bovine kidney (MDBK) cells (Etkind & Krug, 1975, *J. Virology* 16, 1464–1475) were grown in monolayers as described (Katze, et al., 1988, J. Virology 62, 3710). Monolayers of MDBK cells (2×10$^{10}$ cells; 800 T150 flasks) were infected with influenza virus at a multiplicity of infection (m.o.i.) of 10 plaque-forming units per cell for 4 hours. The infected cells were washed twice with ice-cold Hanks' balanced salt solution and lysed in buffer A:50 mM Tris-HCl, pH 7.5, 50 mM KCl, 1 mM dithiothreitol, 2mM MgCl$_2$, aprotinin at 100 g per ml, 1 mM phenylmethylsulfonyl fluoride, 1% Triton X-100. The cytoplasmic extracts were then centrifuged at 100,000×g for 1 hour in a Beckman Ti 70.1 rotor. The supernatant (S100) was fractionated by ammonium sulfate precipitation (40–60%). The ammonium sulfate precipitate was resuspended in buffer B: 20 mM Tris-HCl, pH 7.5, 1 mM EDTA, 0.1 mM phenylmethylsulfonyl fluoride, 5% glycerol supplemented with 100 mM KCl and dialyzed against the identical buffer. The dialyzed sample was applied to a Mono Q HR 10/10 column. Bound proteins were eluted with a 100-ml linear gradient of 100–500 mM KCl in buffer B. Kinase-inhibitory activity was assayed as described in Example 7 below. The kinase inhibitory material elutes at 280 mM KCl. Active fractions are pooled, concentrated by using a Centriprep 30 concentrator (Amicon, Danvers, Mass.), and dialyzed against buffer B containing 25 mM KCl. The dialyzed fraction is applied to a heparin-agarose column and bound material is eluted by sequential application of buffer B containing, respectively, 100, 300, and 500 mM KCl. The kinase inhibitory activity is found in the 300 mM KCl fraction, which is then concentrated and dialyzed against buffer B/25 mM KCl. The dialysate is loaded onto a Mono S HR 5/5 column, and bound material is eluted with buffer B/250 mM KCl. To achieve the final purification, the active Mono S fraction is layered onto a 10–30% glycerol gradient containing buffer B/25 mM KCl. The gradient is centrifuged at 49,000 rpm for 21 hours in a Beckman SW 55 rotor. Fractions are collected, dialyzed, and assayed for kinase inhibitory activity as described below.

b) Cloning of P58 i. Screening of cDNA Library

Three tryptic peptides derived from purified P58 protein were sequenced by microsequencing. One of the sequences (AEAYLIEEMYDEAIGDYETA) was used to design a degenerate oligonucleotide probe (5'-GAA(G)GAA(G)ATGTAT(C)GAT(C)GAA(A)GC-3'). This was used to screen a cDNA library from the MDBK cell line made in the Lambda Zap II vector (Stratagene). Duplicate plaque transfers were made to nylon filters (Hybond-N; Amersham, Arlington Heights, Ill.). Filters were then prehybridized in 5× SSPE (1× SSPE=0.18M NaCl/10 mM NAPO$_4$, pH 7.4, 1 mM EDTA, 1% SDS, 0.2% Ficoll, 0.2% bovine serum albumin, 0.2% polyvinylpyrrolidone), 100 g of sonicated and denatured salmon sperm DNA per ml at 38C. for 4 hours and hybridized with $^{32}$P-5'-end-labeled probe in 6× SSPE, 1% SDS, 100 g of sonicated and denatured salmon sperm DNA per ml at 38C. for 20 hours. Filters were washed in 6× SSPE, 1% SDS twice at room temperature for 10 minutes, once at 38C. for 15 minutes and exposed at −70C. with Kodak X-Omat film with enhancing screens. Positive phage plaques were identified and purified by further rounds of plaque hybridization. The pBluescript plasmid (Stratagene) was excised out in vivo according to the manufacturer's instructions. EcoR I fragments from 4 positive clones were analyzed by Southern blot hybridization using the degenerate oligonucleotide probe P58-3-2 (5'-GCIGTT(C)TCA(G)TAA(G)TCT(C)TG-3; I represents inosine) corresponding to the antisense-strand of a partial amino acid sequence (QDYETA) of the P58. One positive clone containing an insert of 1400 bp was obtained and analyzed by restriction enzyme mapping. After cloning into M13mp18 and M13mp19, the sequence of the P58 cDNA was determined by the dideoxynucleotide chain-termination method using Sequenase 2.0 (United States Biochemical). See SEQ ID No. 17. Sequence data were analyzed using the Genetics Computer Group (GCG) sequence-analysis program version 7.0).

ii. Isolation of the 3' End Region of P58 cDNA

The initial clone isolated contained a long open-reading frame but no termination codon, suggesting that the 3'-end was missing. The missing 3' end region was isolated using RACE-PCR (Rapid Amplification of cDNA endspolymerase chain reaction) as described (Innis, et al., 1990). MDBK poly (A)+mRNA (1 g) was reverse-transcribed using a hybrid primer (5'-GACTCGAGGATCCGAATTC-(T)$_{17}$-3'). The cDNA pool was amplified by RACE-PCR in the presence of adapter primer (5'-GACGCGACCATCCGAATTC-3') and P58 gene-specific primer P58-5 (5'GCTGAAGAGCTCATCAAAG-3') under the conditions as described (Innis, et al., 1990). After identifying the amplified product by Southern blot, the product was isolated from an agarose gel and cloned into M13mp18 and m13mp19 to sequence the amplified region. This allowed reconstruction of the complete P58 cDNA containing 1680 bp. The original 1400 bp cDNA was also used to screen the MDBK cDNA library and pull out another clone of 3140 bp containing the full coding sequence together with 5'- and 3'-UTRs.

c) Expression of P58 Fusion Protein in Bacteria

A unique Nde I site (CATATG) was introduced at the initiating methionine codon of the P58 gene using an in vitro mutagenesis kit (Bio-Rad, Richmond, Calif.) according to the manufacturer's protocol. After site-directed mutagenesis, a 1.6 kb Nde 1-BamH I fragment containing the P58 gene was cloned into the bacterial expression vector pET15b (Novagen, Madison, Wis.). P58 was expressed as a histidine-tagged fusion protein in E. coli BL21 (DE3)pLysS after inducing with 0.2 mM IPTG for 2 hours at 30C. Most of the fusion protein was found in the insoluble fraction. After denaturing this fraction in 6M Guanidium-HCl, the fusion protein was purified using a Ni(II)-column in accordance with the manufacturer's instructions. The purified protein (0.1 mg/ml) was renatured after diluting about 50-fold in the dialysis buffer (20 mM Tris-HCl, pH 7.5, 1 mM DTT, 0.1 mM EDTA, 0.15M NaCl, 20% glycerol) containing 0.1 mg bovine serum albumin per ml and dialyzing in dialysis buffer at 4C. for 6 hours. The renatured protein was aliquoted and stored at −70C.

EXAMPLE 7

Assay for Inhibition by P58

Cell extracts of test cells or fractions isolated during the P58 purification procedure were mixed with a PKR-containing cell extract prepared by disruption of interferon-treated 293 cells with Triton X-100, and incubated for 20 minutes at 30C. The PKR was then immunoprecipitated using an antibody which recognizes the human PKR from 293 cells but not the bovine homologue in influenza virus-infected MDBK cells, the source of the P58. The activity of the immunoprecipitated PKR was then measured using [gamma-$^{32}$P]ATP and exogenously added histones as substrates. To quantitate activity, histones were subjected to polyacrylamide gel electrophoresis and excised from the gel. An additional assay using pure PKR and its natural substrate, eIF-2, was performed as follows. Extracts of test cells or fractions from the purification were preincubated with pure PKR for 10 minutes at 30C. in buffer C (17 mM Tris-HCl, pH 7.5, 75 mM KCl, 0.1 mM EDTA, 1.0 mM diethiothreitol, aprotinin at 8 g per ml, 0.1 mM phenylmethylsulfonyl fluoride, 2 mM MgCl$_2$, 2 mM MnCl$_2$, 0.3 mg of bovine serum albumin per ml, 8% glycerol). Activator poly(I):poly(C) (0.010 g/ml) was then added in the presence of 1 mM [gamma$^{32}$P]ATP (424 Ci/mmol; 1 Ci=37 GBq) and incubation continued for an additional 10 minutes. Finally, 0.5 g of purified eIF-2 was added and incubation was continued for a further 10 minutes at 30C. The reaction was terminated by addition of 2×disruption buffer (160 mM Tris, pH 6.8, 1.0M 2-mercaptoethanol, 4% SDS, 20% (vol/vol) glycerol), the mixture was boiled, and the phosphorylated proteins are analyzed on an SDS/14% polyacrylamide gel.

EXAMPLE 8

Inactivation of PKR by P58

Up to 2 μl of PKR fraction (the exact volume used depends on the degree of purification) was diluted to 10 μl with 50 mM KCl, 20 mM HEPES (pH 7.4), 1.5 mM MgCl$_2$, 0.1 mM EDTA, 1 mM DTT, 10% glycerol and 1 μM PMSF, 0.1 mg bovine serum albumin and 0.1 mg of tRNA per ml. The diluted kinase was added to 20-μl reaction mixtures containing, at final concentrations, 75 mM KCl, 25 mM HEPES, (pH 7.4), 10 mM MgCl$_2$, 1.0 mM dithiothreitol, 0.1 mM EDTA, 0.1 mM ATP, protease inhibitors, and 5 to 10 μCi of [gamma $^{32}$P]ATP (>3,000 Ci/mmol; Dupont, NEN). Reaction mixtures are supplemented as appropriate with reovirus double-stranded (ds) RNA or synthetic dsRNA (e.g. poly I:C) as an activator and P58 as inhibitor. When used in the same reaction, dsRNA and P58 are added simultaneously to the enzyme mix. The reactions are incubated at 30C. for 15–25 min, then filtered through nitrocellulose in a slot-blot or dot-blot apparatus. $^{32}$P incorporated into the PKR by autophosphorylation is quantitated by liquid scintillation counting or by laser densitometry of an exposed autoradiographic film. A typical test series includes the following reactions: a) control reactions with PKR alone or P58 alone; b) control reactions with test compound alone or with either PKR or P58; c) PKR and P58; and d) PKR, P58 and test compound. For test compounds which interfere with binding of P58 inhibitor to PKR, the amount of autophosphorylated PKR detected in reaction (d) is more than that detected in reaction (c).

The recombinant P58, expressed as a histidine fusion protein in *E. coli*, inhibited both the autophosphorylation and eIF-2 phosphorylation activity of PKR. Protein and RNA analysis revealed that P58 is highly conserved across species. Database analysis revealed that P58 contains regions of homology to the DnaJ heat-shock family of proteins and the PKR natural substrate, eIF-2 alpha. P58 also contains nine tandemly arranged 34 amino acid repeats demonstrating that it is a member of the tetratricopeptide repeat (TPR) family of proteins.

P58 itself might have oncogenic potential through its PKR inhibitory activity and that introduction of the P58 gene together with wild-type PKR can abrogate the tumor suppressor properties of PKR much the same way that the mdm-2 oncogene can overcome p53 mediated suppression of transformed cell growth.

EXAMPLE 9

Oncogenesis by Overexpression of P58

Figure 9:
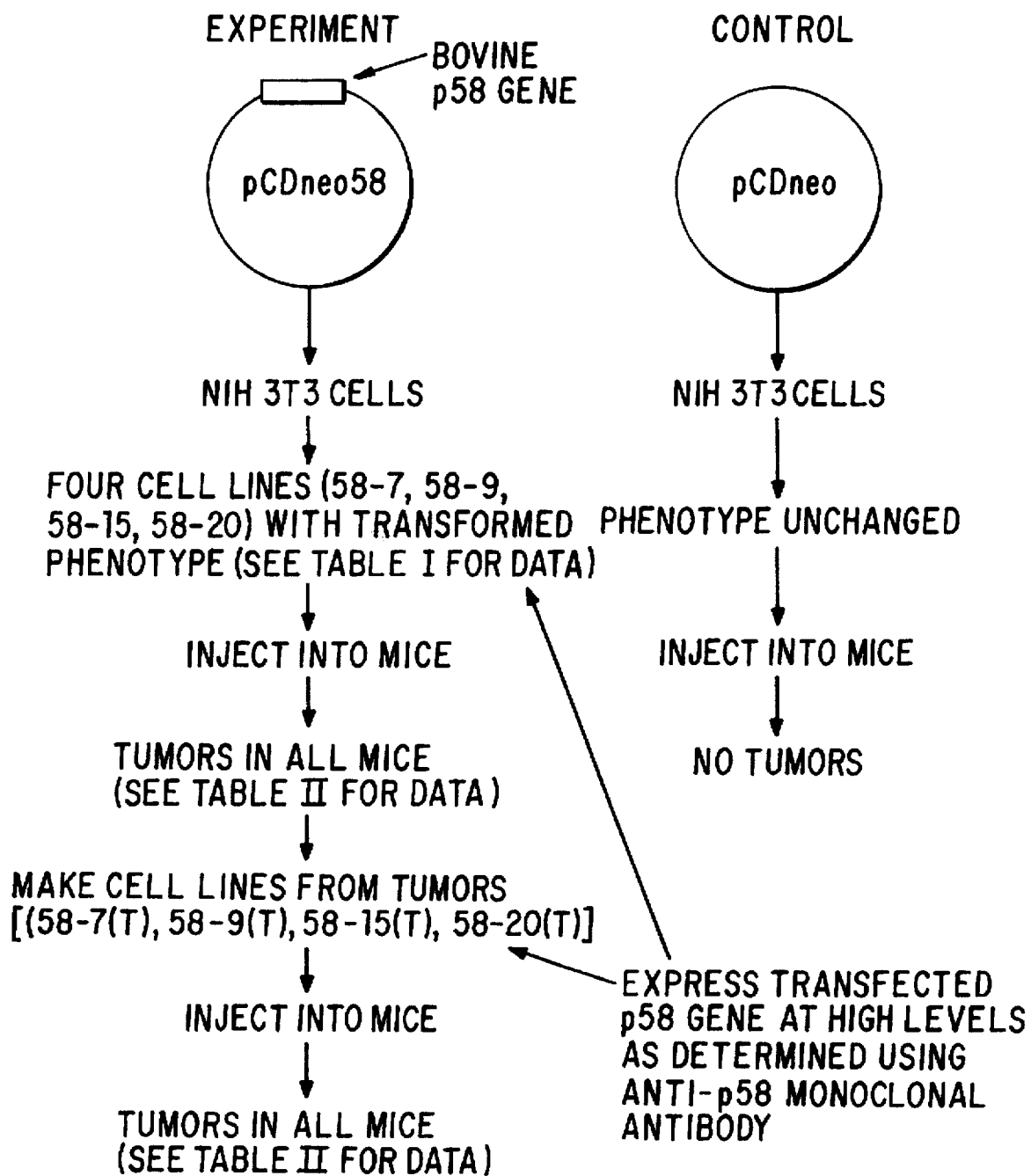
FIG. 9 is a schematic representation of an experiment demonstrating oncogenic properties of P58.

NIH 3T3 cell lines that overexpress the PKR inhibitor P58 were constructed by transfecting cells with the bovine P58 gene subcloned into the pcDNA/neo eukaryotic expression vector by the calcium phosphate coprecipitation technique. Cells were then cultured in medium containing G418 (geneticin). Surviving individual cell clones were then selected for analysis of P58 levels using monoclonal antibody that recognizes the overexpressed bovine but not the endogenous murine P58. At least four independent cell lines which overexpress P58 are identified (see FIG. 9 for a schematic representation of the experiment).

These NIH 3T3 cell lines overexpressing P58 also exhibited a transformed phenotype in terms of in vitro growth characteristics. The cells exhibited accelerated growth rates, an altered morphology, grew to higher densities, and exhibited anchorage independent growth in agar (see Table 1). All four cell lines, when injected into nude mice, produced tumors within approximately 15–21 days (see Table 2). High levels of P58 were detected in the tumors. In addition, cell lines established from the tumors also expressed high levels of P58.

In contrast, nude mice injected with cell lines transfected with vectors lacking the P58 gene did not get tumors.

TABLE 1

Growth Properties of Cells Expressing p58 pCDneo58 (pCDneo containing the bovine p58 gene) was introduced into NIH3T3 cells by calcium phosphate transfection technique. Cells which had taken up the DNA were selected by virtue of their resistance to G418 (geneticin), encoded by the new gene on the vector. Four clones of transformed cells which had received the p58 gene (58-7, 58-9, 58-15, and 58-20) were selected for further study. A clone which had received pCDneo containing no insert ("NEO") was also selected as a control. The in vitro phenotypes of the control and p58-containing cells were assessed by three criteria: doubling time and saturation density when grown in monolayers, and ability to form colonies in soft agar ("cloning efficiency"). See Koromilas et al. parer for details of these assays. The results were as follows:

| Clone | Doubling Time (hours) | Saturation Density (Cells × $10^{-6}$) | Cloning Efficiency (%) |
|---|---|---|---|
| NEO | 28 ± 1.4 | ? | 0 |
| 58-7 | 20 ± 0.5 | 6.0 ± 0.3 | 15.1 |
| 58-9 | 24 ± 1.9 | 4.6 ± 0.4 | 6.4 |
| 58-15 | 23 ± 0.3 | 5.0 ± 0.4 | 8.8 |
| 58-20 | 23 ± 3.5 | 5.5 ± 0.7 | 10.2 |

TABLE 2

Tumorigenicity of Cells Expressing p58

Animals were injected and tumors were scored essentially as described in Koromilas et al. Additionally, fresh cells lines were made from mice and cells from these lines [denoted by the suffix (T)] were injected into mice to test their tumorigenicity.

Two parameters were used to assess tumorigenicity: the number of animals that developed tumors as a fraction of the number injected; and the number of days which elapsed before tumors were detectable.

| Clone | Animals with tumors/ animals injected | Latency (days) |
|---|---|---|
| NEO | 0/9 | — |
| 58-7 | 4/4 | 15–21 |
| 58-9 | 9/9 | 15–21 |
| 58-15 | 4/4 | 26–30 |
| 58-20 | 9/9 | 15–18 |
| 58-7(T) | 2/2 | 7–9 |
| 58-9(T) | 2/2 | 7–9 |
| 58-15(T) | 2/2 | 7–9 |
| 58-20(T) | 2/2 | 7–9 |

E. Assaying Anti-P58 Activity

Anti-P58 activity within test cells may be measured by the ability of cell extract, a fraction of cell extract, or purified anti-P58 protein from cell extract in activating PKR protein kinase activity (i.e., PKR autophosphorylation and/or phosphorylation of eIF-2 by PKR) repressed by P58. In a preferred embodiment, anti-P58 activity is assayed in a purified or partially purified form.

An assay for anti-P58 activity is described by Lee et al., 267 J. Biol. Chem. 14238, 1992. Anti-P58 protein(s) can be purified from the ammonium sulfate fraction containing anti-P58 activity using the method described in Example 6 or other methods recognized by those skilled in the art. Once the anti-P58 protein is purified, anti-P58 gene can be cloned, sequenced, and expressed using the method described in Example 6 or other methods recognized by those skilled in the art.

II. Method for Screening for Anti-tumor Agents

The invention includes methods for screening compounds for anti-tumor activity. Methods to screen potential agents for their ability to inhibit or moderate oncogenesis can be designed without detailed knowledge of the precise mechanism, although such a knowledge can certainly be helpful. In principle, many of the methods which have so far been described to identify neoplastic cells can be readily adapted to detect anti-tumor agents.

Thus, for example, if it has been found that oncogenesis is correlated to a subnormal activity of PKR, or any other observable effect described in the foregoing disclosure, then agents can be screened for their ability to prevent or moderate this effect. The screening can be performed by adding the test agent to intact cells which examine the effect, or by adding the test agent to in vitro enzymatic or hybridization reactions and then proceeding with the established analysis. Where interaction between two or more proteins are necessary for oncogenesis, the screening can be performed by adding the test agent to a system in which the interaction would normally occur, and analyze the impact of the test agent on the interaction.

The assays encompassed by this invention can be used to screen agent libraries to discover novel anti-tumor drugs. Such libraries may comprise either collections of pure agents or collections of agent mixtures. Examples of pure agents include, but are not necessarily limited to, proteins, polypeptides, peptides, nucleic acids, oligonucleotides, carbohydrates, lipids, synthetic or semi-synthetic chemicals, and purified natural products. Examples of agent mixtures include, but are not limited to, extracts of prokaryotic or eukaryotic cells and tissues, as well as fermentation broths and cell or tissue culture supernates. In the case of agent mixtures, the assays are not only used to identify those crude mixtures that possess the desired anti-tumor activity, but also the assays provide the means to purify the anti-tumor principle from the mixture for characterization and development as a therapeutic drug. In particular, the mixture so identified can be sequentially fractionated by methods commonly known to those skilled in the art which may include, but are not limited to, precipitation, centrifugation, filtration, ultrafiltration, selective digestion, extraction, chromatography, electrophoresis or complex formation. Each resulting subfraction can be assayed for anti-tumor activity using the original assay until a pure, biologically active agent is obtained.

In preferred embodiments, the assays designed for detecting anti-tumor activity are used for automated, high-throughput drug discovery screens in conjunction with the above mentioned libraries. The assays are performed in any format that allows rapid preparation and processing of multiple reactions such as in, for example, multi-well plates of the 96-well variety. Stock solutions of the test agents as well as assay components are prepared manually and all subsequent pipetting, diluting, mixing, washing, incubating, sample readout and data collecting is done using commercially available robotic pipetting equipment, automated work stations, and analytical instruments for detecting the signal generated by the assay. Examples of such detectors include, but are not limited to, spectrophotomers, colorimeters, luminometers, fluorometers, and devices that measure the decay of radioisotopes.

In another embodiment, the assays may be used to screen vast libraries of random peptides or oligonucleotides produced by any of the techniques already in the public domain or otherwise known to those skilled in the art. Because of their large size, these libraries are likely sources of lead agents since they can contain from $10^7$–$10^{10}$ chemical entities. Screening libraries of this size requires allowing test agents to bind to a molecular target in vitro, trapping the resulting complex in order to identify the specific lead agents that have been bound, and then producing the lead) agents in greater quantities for further development.

A. PKR activity

In one method, compounds which exert direct effects on PKR activity are tested, by adding a test compound to be screened to a purified PKR characterized by a subnormal activity of PKR, determining the activity of PKR in the presence of the compound, and selecting the compound if the measured activity of PKR is increased. Such PKR activity can be assessed by measuring autophosphorylation of the PKR molecule, as described in Example 1, or by measuring phosphorylation of a selected PKR substrate, such as eIF-2, detailed in Example 2. Increased PKR phosphorylation activity is measured in these assays by an increase in $^{32}$P-phosphorous incorporation into the target substrate molecule.

Additionally, in order to screen for compounds which exert their PKR activating activity by cellular mechanisms, PKR activity can be measured in intact cells. In one method, cells are incubated with inorganic $^{32}$P-phosphate, in order to label endogenous stores of ATP. Cells are then treated with test compounds, and levels of phosphorylation of substrates PKR and/or eIF-2 are assessed following specific immunoprecipitation of the substrates, according to the immunoprecipitation general methods described in Examples 1 and 2.

A second exemplary method for measuring effects of test compounds on endogenous PKR activity is a "back-phosphorylation assay." Here, cells are exposed to a test compound or control carrier substance. Cells are then lysed under conditions which "freeze" phosphorylation/dephosphorylation reactions in the cell, such as under conditions of acid extraction or high concentrations of zinc ions. PKR is then immunoprecipitated, and the immunoprecipitate subjected to autophosphorylation conditions using radiolabeled ATP, as described in Example 1. In this assay reduced incorporation of $^{32}$P-phosphate into the PKR molecule, compared to control, indicates an increased level of cellular PKR activity.

A third exemplary method for measuring effects of test compounds on endogeneous PKR is a "transformed-cell line assay." Here, cell lines that have been transformed by a mutant PKR are exposed to a test compound or control carrier substance. In this assay, reduced or arrested growth of said transformed cell lines indicates said test compound being an effective anti-tumor agent. This assay uses the methodology described in Koromilas et al., 1992, supra and Meurs et al., 1993 supra, and methods known to those skilled in the art.

A fourth exemplary method for measuring effects of test compounds on endogeneous PKR is a "nude mice assay." Here, the transformed cell lines described in the above paragraph are injected to nude mice to produce tumor. The injected nude mice are exposed to a test compound or control carrier substance. Delayed tumor growth or elimination of tumor in the nude mice indicates the test compound being an effective anti-tumor agent. This assay uses the methodology described in Koromilas et al., 1992, supra, and Meurs et al., 1993, supra, and methods known to those skilled in the art.

Generally, in any of the assays described above, a test compound is selected, if exposure of cells to the compound results in an increase in autophosphorylation of PKR or an increase in phosphorylation of eIF-2.

B. P58 activity

Compounds that reduce or inhibit P58 activity can also be effective anti-tumor agents.

In one exemplary method, compounds which suppress P58 activity are tested by adding a test compound to a mixture in which the PKR activity is repressed by P58, determining the activity of PKR in the presence of the compound, and selecting the compound if the measured activity of PKR is increased. The activity of PKR can be measured by the methods described above in A.

A second exemplary method for measuring effects of test compounds on P58 is a "transformed-cell line assay." Here, cell lines that have been transformed by overexpression of P58, such as those described in Example 8, are exposed to a test compound or control carrier substance. In this assay, reduced or arrested growth of said transformed cell lines indicates the test compound being an effective anti-tumor agent. This assay uses the methodology described in Koromilas et al., 1992, supra, and Meurs et al., 1993, supra, and methods known to those skilled in the art.

A third exemplary method for measuring effects of test compounds on P58 is a "nude mice assay." Here, the transformed cell lines described in the above paragraph are injected to nude mice to produce tumor. The injected nude mice are exposed to a test compound or control carrier substance. Delayed tumor growth or elimination of tumor in said nude mice indicates said test compound being an effective anti-tumor agent. This assay uses the methodology described in Koromilas et al., 1992, supra, and Meurs et al., 1993, supra, and methods known to those skilled in the art.

C. Interaction between PKR and P58

P58 does not function as a protease, phosphatase, or ATPase. Furthermore, P58 does not degrade or sequester dsRNAs nor does it compete for dsRNA binding sites. It is likely that P58 inhibits PKR through a direct interaction since P58 blocks both the autophosphorylation of PKR in addition to the phosphorylation of the eIF-2 alpha subunit.

Binding interactions between two or more components can be measured in a variety of ways. One approach is to label one of the components with an easily detectable label, place it together with the other component(s) in conditions under which they would normally interact, perform a separation step which separates bound labeled component from unbound labeled component, and then measure the amount of bound component. The effect of a test agent included in the binding reaction can be determined by comparing the amount of labeled component which binds in the presence of this agent to the amount which binds in its absence.

The separation step in this type of procedure can be accomplished in various ways. In one approach, (one of) the binding partner(s) for the labeled component can be immobilized on a solid phase prior to the binding reaction, and unbound labeled component can be removed after the binding reaction by washing the solid phase. Attachment of the binding partner to the solid phase can be accomplished in various ways known to those skilled in the art, including but not limited to chemical cross-linking, non-secific adhesion to a plastic surface, interaction with an antibody attached to the solid phase, interaction between a ligand attached to the binding partner (such as biotin) and a ligand-binding protein (such as avidin or streptavidin) attached to the solid phase, and so on.

Alternatively, the separation step can be accomplished after the labeled component had been allowed to interact with its binding partner(s) in solution. If the size differences between the labeled component and its binding partner(s) permit such a separation, the separation can be achieved by passing the products of the binding reaction through an ultrafilter whose pores allow passage of unbound labeled component but not of its binding partner(s) or of labeled component bound to its partner(s). Separation can also be achieved using any reagent capable of capturing a binding partner of the labeled component from solution, such as an antibody against the binding partner, a ligand-binding protein which can interact with a ligand previously attached to the binding partner, and so on.

Besides examining the impact of these agents on the interaction between two or more components in in vitro reactions, the interacting components can also be brought into contact with one another within cells rather than in in vitro reactions. In this approach, coding sequence(s) encoding part or all of a component or components would be introduced into a selected type of cell. Coding sequences for this approach include cloned genes or cDNAs or fragments of either or fragments amplified by the polymerase chain reaction or natural RNAs or transcribed RNAs or the like. Several variations of the approach are possible. In one variation, a coding sequence is introduced for a first component into a cell known to contain components with which this first component will interact. Agents are tested to select those which block the effect of interaction between the first component and the cellular component. In another variation, coding sequences for two or more components which interact with one another might be introduced into a cell, and agents tested for their ability to moderate the interaction between these components, this interaction being followed by the procedures previously established as suitable for the purpose. The cell into which the coding sequences are introduced can be one which is easy to grow, manipulate and test such as a yeast cell. Indeed, there are distinct advantages to reconstructing a translation control mechanism in heterologous cells, in which the interactions between the components involved are easier to study than they are when those components are in their normal environment. In the case of yeast, in particular, the powerful genetic approaches available often make it possible to identify and isolate the yeast homologues of genes from higher eukaryotes more quickly than the corresponding genes can be identified in the higher eukaryotes.

EXAMPLE 10

Preparing PKR (a) From Interferon-Induced Human Cells

PKR is prepared from interferon-induced human tissue culture cell lines. Cells are lysed by Dounce homogenization, and nuclei and cell debris removed by centrifugation at 30,000×g for 20 minutes. 4M KCl is added to the supernatant to a final concentration of 100 mM, and ribosomes are pelleted by centrifugation at 60,000 rpm in Beckman type 60 rotor. The ribosomal pellet is resuspended in 800 mM KCl, 20 mM HEPES (pH 7.4), 1.5 mM $MgCl_2$, 0.1 mM EDTA, 1 mM DTT and 1M phenylmethylsulfonyl fluoride (PMSF), then homogenized using a Dounce homogenizer. The ribosomes are then centrifuged again at 60,000 rpm for 90 min at 4C. in a type 60 rotor. The resulting supernatant is dialyzed against 50 mM KCl, 20 mM HEPES (pH 7.4), 1.5 mM $MgCl_2$, 0.1 mM EDTA, 1 mM DTT, 10% glycerol and 1M PMSF. The dialysate is centrifuged again to remove solids. The resulting supernatant (ribosomal salt wash) is applied to a DEAE-cellulose column equilibrated in 50 mM KCl, 20 mM HEPES (pH 7.4), 1.5 mM $MgCl_2$, 0.1 mM EDTA, 1 mM DTT, 10% glycerol and 1M PMSF. PKR is collected in the flowthrough fraction, adjusted to pH 6.8, and applied to a S-Sepharose Fast Flow (Pharmacia) column equilibrated with 50 mM KCl, 20 mM HEPES (pH 6.8), 1.5 mM $MgCl_2$, 0.1 mM EDTA, 1 mM DTT, 10% glycerol and 1M PMSF. PKR is eluted from the column in a linear gradient of 50–500 mM KCl in 20 mM HEPES (pH 7.4), 1.5mM MgCl$_2$, 0.1 mM EDTA, 1 mM DTT, 10% glycerol and 1M PMSF. The PKR peak is loaded onto a hydroxyapatite HPHT (BioRad) column equilibrated in 50 mM KCl, 20 mM HEPES (pH 7.2), 50 mM potassium phosphate (pH 7.2), 1.5 mM MgCl$_2$, 0.1 mM EDTA, 1 mM DTT, 10% glycerol and 1M PMSF. PKR is eluted in a linear gradient of 50–500 mM potassium phosphate (pH 7.2). The PKR peak is loaded to an HR 5/10 Mono S column (Pharmacia) and eluted in a linear gradient of 50–500 mM KCl in 20 mM HEPES (pH 7.4), 1.5mM MgCl$_2$, 0.1 mM EDTA, 1 mM DTT, 10% glycerol and 1M PMSF. The purified PKR is stored at –70C.

(b). From Recombinant *E. coli* Cells

Alternatively, PKR is purified from *E. coli* expressing human PKR, according to published methods (Barber et al., 1991, *Biochemistry* 30:10356). Briefly, *E. coli* strain BL21 (DE3) pLysS is transformed with a plasmid containing the coding sequence for wild-type PKR under the control of an inducible promoter. The resulting *E. coli* strain is grown to log phase, then induced to express PKR. Cells are harvested by centrifugation, and lysed by lysozyme. PKR is purified from the lysate by affinity chromatography using a monoclonal antibody to PKR coupled to Sepharose, according to published methods (Galabru et al., 1989, *Eur. J. Biochem.* 178:581).

EXAMPLE 11

Slot-Blot Filter-Binding Assay

Reaction mixtures containing one or more of purified radiolabeled P58, purified PKR, and test compound are incubated together for 15–20 minutes on ice in the presence of 75 mM KCl, 25 mM HEPES, (pH 7.4), 10 mM MgCl$_2$, 1.0 mM dithiothreitol, 0.1 mM ATP, 0.1 mg/ml bovine serum albumin, 0.1 mM tRNA and 0.1 mM EDTA. Reactions are diluted with 10 volumes of wash buffer (50 mM KCl, 1.5 mM MgCl$_2$, 20 mM HEPES (pH 7.4), 0.1 mM EDTA), and immediately filtered in a slot-blot apparatus through a 0.45 micron pore-size nitrocellulose membrane (Schleicher & Schuell, Keene, N.H.) that has been soaked for 1 hour at room temperature in wash buffer containing 0.1 mg each of BSA and salmon sperm DNA per ml. Each well is washed with 200 l of ice-cold wash buffer, and the filter is dried and exposed to autoradiography. Quantitation is performed by scintillation counting of individual bands or by direct scanning of the membrane with a AMBIS Imaging System. A typical test series includes the following reactions: a) control reactions with PKR alone or P58 alone; b) control reactions with test compound alone or with either PKR or P58; c) PKR and P58; and d) PKR, P58 and test compound. For test compounds which interfere with binding of P58 to PKR, the amount of bound P58 detected in reaction (d) is less than that detected in reaction (c).

III. Tumor-Cell Therapy

The invention includes methods for treating human neoplasms which are characterized by either a subnormal activity of PKR or anti-P58 or an above normal activity of P58. The method includes introducing into the neoplastic cells a source of PKR activity or/and a source of anti-P58 activity.

A. Introduction of Wild Type PKR Coding Sequence to Neoplastic Cells

The wild type PKR gene or a part of the gene may be introduced into the cell in a vector, such that the gene remains extrachromosomal. Evidence that active PKR is a dimer of two PKR subunits has been presented, and it has been suggested that dimerization of a mutant subunit with a wildtype subunit results in an inactive molecule. Extrachromosomally produced wildtype PKR will bind and saturate mutant PKR as well as form active dimers with other wildtype molecules, to restore normal PKR activity to the cell.

Alternatively, the wildtype PKR gene may be introduced into cells in such a way that it recombines with the endogenous mutant PKR gene present in the cell. Such recombination would require a double recombination event which would result in the correction of the PKR gene mutation.

Known in the medical literature are manipulations for introducing genes into cells. Such "gene therapy" has been particularly successful in treatment of blood lymphocytes (Culver) and is the subject of a high level of current investigation for delivering genes to bone marrow cells. Generally within the reach of current techniques of gene therapy are those neoplastic cell populations that can be removed from a patient, transduced with a vector containing the insertion gene, then replaced or re-transplanted into the patient.

It can be appreciated that the current invention will include gene therapy with a wildtype PKR gene as an insertion gene, in order to restore PKR activity to cells, such as neoplastic cells, having mutant PKR activity. Methods for introducing such genes are known in the art (Culver, Mikisch). Generally such methods include first removing the cells from the subject and establishing the cells in culture for expansion and transduction with the insertion gene. The insertion cDNA represents the full-length coding region for PKR present in a retroviral vector, such as a Moloney murine leukemia virus-based retroviral vector having a Neo$^R$ selection gene. The presence of the selection gene aids in selection of successfully transduced cells for re-transplantation into the subject. Following transduction of cells with the PKR cDNA, such cells are replaced in the patient.

B. Introduction of PKR Protein to Neoplastic Cells

Polypeptides or other molecules which have PKR activity may be supplied to cells which carry mutant PKR alleles. The active molecules can be introduced into the cells by microinjection or by liposomes, or by electroporation methods, for example. Alternatively, some such active molecules may be taken up by the cells, actively or by diffusion, to restore PKR activity to the cells.

C. Introduction of Anti-P58 Activity to Neoplastic Cells

The wild type anti-P58 coding sequence and wild type anti-P58 protein, or portions or segments of them, may be introduced to neoplastic cells using the methods described in A and B above.

D. Administation of agents

In practicing the methods of the invention, the compositions, such as those discussed in A, B, and C above, can be used alone or in combination with one another, or in combination with other therapeutic or diagnostic agents. These compositions can be utilized in vivo, ordinarily in a mammal, preferably in a human, or in vitro. In employing them in vivo, the compositions can be administered to the mammal in a variety of ways, including parenterally, intravenously, subcutaneously, intramuscularly, colonically, rectally, vaginally, nasally, orally, transdermally, topically, ocularly, intraperitoneally, or as suitably formulated surgical implants employing a variety of dosage forms. As will be readily apparent to one skilled in the art, the useful in vivo dosage to be administered and the particular mode of administration will vary depending upon the mammalian species treated, the particular composition employed, and the specific use for which these compositions are employed. The determination of effective dosage levels, that is the dosage levels necessary to achieve the desired result, will be within the ambit of one skilled in the art. Typically, applications of compositions are commenced at lower dosage levels, with dosage level being increased until the desired effect is achieved.

The dosage for the compositions of the present invention can range broadly depending upon the desired affects and the therapeutic indication. Typically, dosages will be between about 0.01 g and 100 mg/kg, preferably between about 0.01 and 10 mg/kg, body weight. Administration is preferably per os on a daily or as-needed basis.

Orally-administered formulations can be prepared in conventional forms, including capsules, chewable tablets, enteric-coated tablets, syrups, emulsions, suspensions, or as solid forms suitable for solution or suspension in liquid prior to administration. Suitable excipients are, for example, water, saline, dextrose, mannitol, lactose, lecithin, albumin, sodium glutamate, cysteine hydrochloride or the like. In addition, if desired, the pharmaceutical compositions may contain minor amounts of nontoxic auxiliary substances, such as wetting agents, pH buffering agents, and the like. If desired, absorption enhancing preparations (e.g., liposomes) may be utilized.

In selected cases, drug delivery vehicles may be employed for systemic or topical administration. They can be designed to serve as a slow release reservoir, or to deliver their contents directly to the target cell. An advantage of using direct delivery drug vehicles is that multiple molecules are delivered per vehicle uptake event. Such vehicles have been shown to also increase the circulation half-life of drugs which would otherwise be rapidly cleared from the blood stream. Some examples of such specialized drug delivery vehicles which fall into this category are liposomes, hydrogels, cyclodextrins, biodegradable polymers (surgical implants or nanocapsules), and bioadhesive microspheres.

For example, a liposome delivery vehicle originally designed as a research tool, Lipofectin, has been shown to deliver intact molecules to cells. Liposomes offer several advantages: They are non-toxic and biodegradable in composition; they display long circulation half-lives; and recognition molecules can be readily attached to their surface for targeting to tissues. Finally, cost-effective manufacture of liposome-based pharmaceuticals, either in a liquid suspension or lyophilized product, has demonstrated the viability of this technology as an acceptable drug delivery system.

Other controlled release drug delivery systems, such as nonoparticles and hydrogels may be potential delivery vehicles for an agent. These carriers have been developed for chemotherapeutic agents.

Topical administration of agents is advantageous since it allows localized concentration at the site of administration with minimal systemic adsorption. This simplifies the delivery strategy of the agent to the disease site and reduces the extent of toxicological characterization. Furthermore, the amount of material to be administered is far less than that required for other administration routes.

Effective delivery requires the agent to diffuse into the infected cells. Chemical modification of the agent may be all that is required for penetration. However, in the event that such modification is insufficient, the modified agent can be co-formulated with permeability enhancers, such as Azone or oleic acid, in a liposome. The liposomes can either represent a slow release presentation vehicle in which the modified agent and permeability enhancer transfer from the liposome into the infected cell, or the liposome phospholipids can participate directly with the modified agent and permeability enhancer in facilitating cellular delivery.

Agents may also be systemically administered. Systemic absorption refers to the accumulation of drugs in the blood stream followed by distribution throughout the entire body. Administration routes which lead to systemic absorption include: oral, intravenous, subcutaneous, intraperitoneal, intranasal, intrathecal and ocular. Each of these administration routes exposes the agent to an accessible diseased tissue. Subcutaneous administration drains into a localized lymph node which proceeds through the lymphatic network into the circulation. The rate of entry into the circulation has been shown to be a function of molecular weight or size. The use of a liposome or other drug carrier can localize the agent at the lymph node and participate in the delivery of the agent to the cell.

A formulation which can associate agents with the surface of lymphocytes and macrophages is also useful. This will provide enhanced delivery to, for example, HSV-infected cells by taking advantage of the specificity of macrophage and lymphocyte immune recognition of infected cells.

Intraperitoneal administration also leads to entry into the circulation with the molecular weight or size of the agent-delivery vehicle complex controlling the rate of entry.

Liposomes injected intravenously show accumulation in the liver, lung and spleen. The composition and size can be adjusted so that this accumulation represents 30% to 40% of the injected dose. The rest is left to circulate in the blood stream for up to 24 hours.

All publications referenced herein are hereby incorporated by reference herein, including the nucleic acid sequences listed in each publication.

Other embodiments are within the following claims.

---

What is claimed is:

1. A method for screening for anti-tumor agent, comprising the steps of:
   providing a system containing PKR activity;
   contacting said system with a test agent;
   measuring PKR activity before and after the addition of said agent, wherein an increase in said PKR activity is indicative of said agent being an effective anti-tumor agent.

2. The method of claim 1 further comprising providing P58 to reduce the level of PKR activity in the absence of a test agent in said system.

3. The method of claim 1, wherein said system comprises a transformed cell line having a mutant PKR gene, which produces an abnormal PKR.

4. The method of claim 3, wherein said measuring comprises detecting the reduction or arrest of growth of said transformed cell line.

5. The method of claim 1, wherein said system comprises a nude mouse injected with a cell containing a mutant PKR gene, which produces an abnormal PKR.

6. The method of claim 1, wherein said system comprises a transformed cell line having an above normal level of P58 expressed from a cloned gene.

7. The method of claim 6, wherein said measuring comprises detecting the reduction or arrest of growth of said transformed cell line.

8. The method of claim 1, wherein said system comprises a nude mouse injected with a cell expressing above normal level of P58.

9. The method of claim 8 or 5, wherein said measuring comprises detecting delay or prevention of tumor growth in said nude mice.

* * * * *